US012747222B2

(12) United States Patent
Shabat et al.

(10) Patent No.: US 12,747,222 B2
(45) Date of Patent: Sep. 29, 2026

(54) CHEMILUMINESCENCE PROBES FOR TUBERCULOSIS

(71) Applicants: Ramot at Tel-Aviv University Ltd., Tel Aviv (IL); The Board of Trustees of the Leland Stanford Junior University, Stanford, CA (US)

(72) Inventors: Doron Shabat, Tel Aviv (IL); Ori Green, Tel Aviv (IL); Matthew Bogyo, Redwood City, CA (US)

(73) Assignees: Ramot at Tel-Aviv University Ltd., Tel Aviv (IL); The Board of Trustees of the Leland Stanford Junior University, Stanford, CA (US)

( * ) Notice: Subject to any disclaimer, the term of this patent is extended or adjusted under 35 U.S.C. 154(b) by 888 days.

(21) Appl. No.: 17/904,527

(22) PCT Filed: Feb. 17, 2021

(86) PCT No.: PCT/IL2021/050184
§ 371 (c)(1),
(2) Date: Aug. 18, 2022

(87) PCT Pub. No.: WO2021/165959
PCT Pub. Date: Aug. 26, 2021

(65) Prior Publication Data

US 2023/0094870 A1 Mar. 30, 2023

Related U.S. Application Data

(60) Provisional application No. 62/978,456, filed on Feb. 19, 2020.

(51) Int. Cl.
*C07D 321/00* (2006.01)
*C12Q 1/04* (2006.01)
*C12Q 1/18* (2006.01)

(52) U.S. Cl.
CPC ............ *C07D 321/00* (2013.01); *C12Q 1/04* (2013.01); *C12Q 1/18* (2013.01)

(58) Field of Classification Search
CPC ..................................................... C07D 321/00
See application file for complete search history.

(56) References Cited

FOREIGN PATENT DOCUMENTS

WO 2019224338 A1 11/2019

OTHER PUBLICATIONS

Chi et al; "Intraoperative Imaging-Guided Cancer Surgery: From Current Fluorescence Molecular Imaging Methods to Future Multi-Modality Imaging Technology" Theranostics 4 (11), pp. 1072-1084. (2014).

Hananya et al: "Rapid chemiexcitation of phenoxy-dioxetane luminophores yields ultrasensitive chemiluminescence assays". Chemical Science, 10(5), pp. 1380-1385. (2019).

Lentz et al; . "Design of Selective Substrates and Activity-Based Probes for Hydrolase Important for Pathogenesis 1 (HIP1) from *Mycobacterium tuberculosis*" ACS Infection Diseases, 2, pp. 807-815. (2016).

Mieog et al; "Toward Optimization of Imaging System and Lymphatic Tracer for Near-Infrared Fluorescent Sentinel Lymph Node Mapping in Breast Cancer". Annals of surgical oncology 18, pp. 2483-2491. (2011).

Troyan et al; "The FLARE™ Intraoperative Near-Infrared Fluorescence Imaging System: A First-in-Human Clinical Trial in Breast Cancer Sentinel Lymph Node Mapping" Annals of surgical oncology 16, pp. 2943-2952. (2009).

International Search Report and Written Opinion issued in International Application No. PCT/IL2021/050184, mailed on May 24, 2021.

*Primary Examiner* — John S Kenyon
(74) *Attorney, Agent, or Firm* — Knobbe, Martens, Olson & Bear, LLP

(57) ABSTRACT

Turn-ON dioxetane-based chemiluminescence probes based on the Schapp's adamantylidene-dioxetane probe are useful for determining the presence, or measuring the level, of *Mycobacterium tuberculosis* (Mtb)-specific protease in a sample, and for assessing the susceptibility of the Mtb to an antibiotic drug. determining the presence or measuring the level of *Mycobacterium tuberculosis* (Mtb)-specific protease in the sample can include contacting the sample with a certain compound, and imaging the sample to detect an emission of light.

26 Claims, 5 Drawing Sheets

Fig. 4A

| Species | Identity | Ser 228 | Asp 463 | His 490 |
|---|---|---|---|---|
| *M. tuberculosis* | | TYLGY**S**YGTRI | VSTTH**D**PATPY | FDGTQ**H**TVVFQ |
| *M. kansasii* | 89% | TYLGY**S**YGTRI | VSTTH**D**PATPY | FNGTQ**H**TVVFQ |
| *M. gordonae* | 86% | TYLGY**S**YGTRI | VSTTH**D**PATPY | YNGTQ**H**TVVFQ |
| *M. intracellulare* | 85% | TYLGY**S**YGTRI | VSTTH**D**PATPY | YDGTQ**H**TVVFQ |
| *M. scrofulaceum* | 85% | TYLGY**S**YGTRI | VSTTH**D**PATPY | YDGTQ**H**TVVFQ |
| *M. avium* | 84% | TYLGY**S**YGTRI | VSTTH**D**PATPY | YDGTQ**H**TVVFQ |
| *M. chelonae* | 70% | NYLGY**S**YGTRI | VSTTN**D**PATPY | YEGTQ**H**TVVFQ |
| *M. abscessus* | 68% | TYLGY**S**YGTRI | VSTVH**D**PATPY | FDGTQ**H**TVVFQ |
| | | .********** | ***.:****** | : ********* |

Fig. 4B

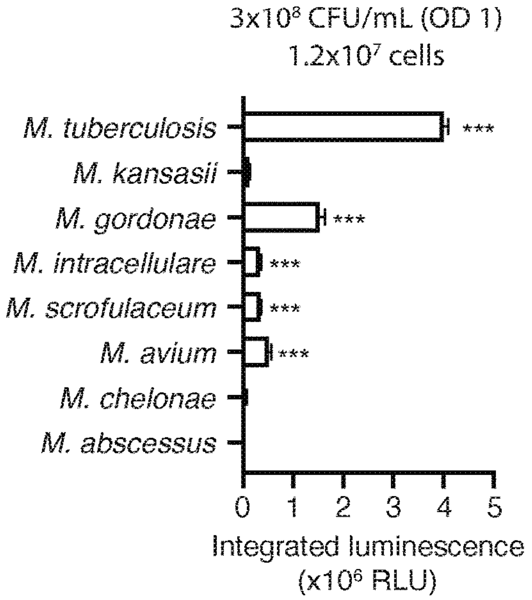

Fig. 4C

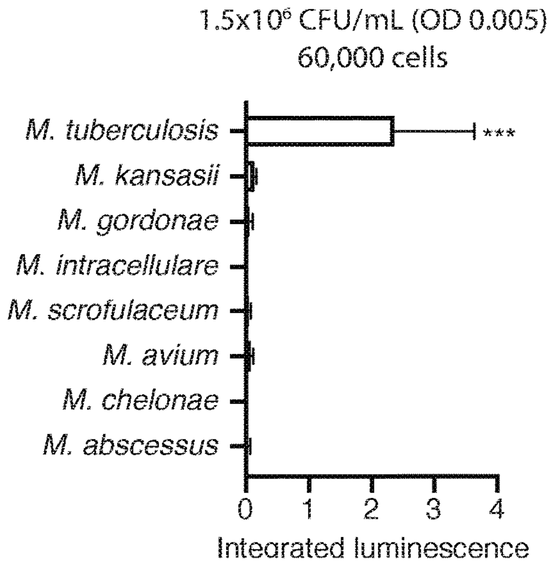

CHEMILUMINESCENCE PROBES FOR TUBERCULOSIS

GOVERNMENT RIGHTS

This invention was made with the United States (US) government support under contract No. EB026332 awarded by the US National Institute of Health. The US government has certain rights in this invention.

TECHNICAL FIELD

The present invention provides extremely bright dioxetane-based chemiluminescence probes capable of detecting *Mycobacterium tuberculosis*, as well as compositions and uses thereof.

Abbreviations: ACN, acetonitrile; DCM, dichloromethane; DIPEA-N,N-diisopropylethylamine; DMBA, 1,3-dimethylbarbituric acid; DMF, N,N'-dimethylformamide; DMSO, dimethyl sulfoxide; EEDQ, N-ethoxycarbonyl-2-ethoxy-1,2-dihydroquinoline; EtOAc, ethylacetate; Fmoc, fluorenylmethoxycarbonyl; HATU, 1-[bis(dimethylamino) methylene]-1H-1,2,3-triazolo[4,5-b]pyridinium 3-oxide hexafluorophosphate; HBTU, hexafluorophosphate benzotriazole tetramethyl uronium; Hex, hexane; HPLC, high pressure liquid chromatography; $K_2CO_3$, potassium carbonate; $Na_2SO_4$, sodium sulfate; PBS, phosphate-buffered saline; RLU, relative light units; RP-HPLC, reverse-phase high pressure liquid chromatography; TFA, trifluoroacetic acid; THF, tetrahydrofuran; TLC, thin layer chromatography; TMSCl, trimethylsilyl chloride.

BACKGROUND ART

*Mycobacterium tuberculosis* (Mtb) is an infectious agent that has over 10 million new cases per year, and nearly a billion current latent infections, and causes over a million deaths per year. As such, there is a need for new methods to rapidly and effectively diagnose infections, especially in resources-limited areas where infection is prevalent. Current methods for diagnosis involve analysis of sputum samples by microscopy or use of polymerase chain reaction (PCR)-based screening tests to confirm the presence of the bacteria. However, these methods require access to specialized equipment and/or personnel with specialized medical training to make a diagnosis. Final confirmation of infection involves the use of the current gold standard culture analysis which requires days to weeks due to the slow growth rate of the bacteria. Furthermore, due to the rise in rates of antibiotic resistance, there is a need to perform analysis of antibiotic susceptibility of clinical isolates. Currently, this analysis requires measurement of the impact of multiple drugs on growth over days to weeks, thus preventing rapid treatment. There is thus an urgent need for rapid, inexpensive and reliable methods for both diagnosing infection and assessing response to diverse antibiotics.

Lentz et al. (2016) discloses selective substrates and activity-based luminescent probes for Hydrolase Important for Pathogenesis 1 (Hip1) serine protease from Mtb. The probes disclosed are composed of a chloroisocoumarin scaffold that irreversibly inhibits Hip1, to which a selective substrate consisting of a 4-mer peptide is linked via an amide bond. Using various methods, including a hybrid combinatorial substrate library profiling method, the high degree of substrate specificity of Hip1 for a P2 lysine (with a preference for this natural residue over all other non-natural analogs including lysine analogs) has been confirmed. As further found, several non-natural aromatic amino acids were accepted in the P3 position with the most effective cleavage observed for L-4-chloro-phenylalanine (4ClPhe). In the P4 position, L-indanylglycine (L-Igl) and L-(benzyl) cysteine showed a 3- to 4-fold higher cleavage than for any of the natural amino acids, suggesting that this position could be used to increase the specificity and turnover rates of selective Hip1 substrates. Using a combination of all the profiling data, an optimized Hip1 substrate containing the L-amino acid sequence acetyl-Igl-4ClPhe-Lys-Leu was designed.

Although fluorescence imaging allows for sensitive monitoring, it has disadvantages, mostly due to auto-fluorescence leading to a low signal-to-noise ratio. Unlike fluorescence-based assays, chemiluminescence assays require no light excitation, resulting in added sensitivity and increased signal-to-noise ratio.

Amongst known chemiluminescence probes, Schaap's adamantylidene-dioxetane probes are with highest applicability, as they bear a stable dioxetane moiety making them suitable for many chemical and biological conditions. These probes are equipped with an analyte-responsive protecting group used to mask the phenol moiety of the probe. Removal of the protecting group by the analyte of interest generates an unstable phenolate-dioxetane species, which decomposes through a chemiexcitation process to produce adamantanone and an excited intermediate benzoate ester that decays to its ground-state through emission of a blue light photon.

Richard et al. (2007) developed turn-ON chemiluminescence probes, bearing a protease (penicillin g-amidase or caspase-3) responsive substrate masking the phenol of the dioxetane luminophores. Although these probes show prominent signal-to-noise ratio, they prohibit live cell-imaging of proteases, as they require a two-step assay. First, the protease cleaves the protecting group in physiological pH (7.4) and then the mixture is added to a buffer with a pH of 12.3, which allows for the chemiexcitation process to occur.

WO 2017/130191 discloses turn-ON chemiluminescence probes based on the Schapp's adamantylidene-dioxetane probe, wherein said probe is substituted at the ortho position of the phenolic ring with a π* acceptor group such as an acrylate and acrylonitrile electron-withdrawing group so as to increase the emissive nature of the benzoate species (Scheme 1). As shown, the chemiluminescence probes disclosed allow for the enzymatic hydrolysis and the chemiexcitation process to occur concurrently under physiological conditions, with remarkable chemiluminescence intensities.

Scheme 1: Direct chemiluminescence mode obtined by substituting the Schapp's adamantylidene-dioxetane probe with a π* acceptor group (WO 2017-130191)

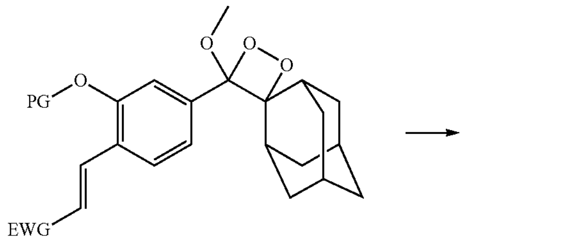

-continued

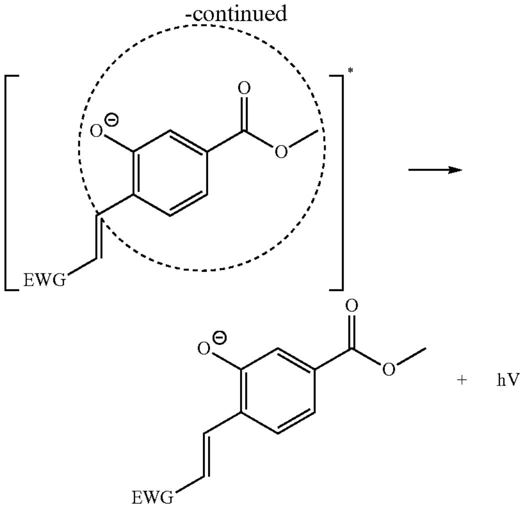

PG — Protecting Group
EWG — Electron Withdrawing Group

WO 2018/216012 discloses chemiluminescence probes based on those disclosed in WO 2017/130191 and constructed with protease cleavable substrates, which upon enzymatic degradation reveal dioxetane luminophores capable of emitting a chemiluminescent signal. Said probes include a dioxetane luminophore that can be adapted with different halogens, changing the pKa of the luminophore, and an electron withdrawing group, yielding a donor-acceptor pair which gives a strong chemiliminescent signal, allowing for the probes to be used under aqueous conditions. WO 2019/224338 discloses similar chemiluminescence probes, which are constructed with cleavable analyte-responsive groups that make them useful for detection of target microorganisms, preferably bacteria.

WO 2018/216013 discloses chemiluminescence probes in which the conjugated electron π-system of the probe disclosed in WO 2017/130191 is further extended in such manner that produces a near-infrared (NIR) donor-acceptor pair. The probes disclosed thus emit light in the NIR region and are therefore useful for in vivo imaging. Additional long wavelength emitting chemiluminescent probes based on those of WO 2017/130191 are disclosed in WO 2019/224339.

SUMMARY OF INVENTION

The present invention provides turn-ON dioxetane-based chemiluminescence probes based on those disclosed in the various International Publications mentioned above, having Mtb-specific protease cleavable peptide, based on the selective peptide substrates of Lentz et al. (2016), as the cleavable group. As shown herein, upon exposure of such probes to Hip1, i.e., enzymatic degradation, dioxetane luminophores capable of emitting a chemiluminescent signal are formed. These luminophores exhibit extremely high chemiluminescence quantum-yield under physiological conditions, and the chemiexcitation kinetics of said luminophores is very slow ($t_{1/2}$>10 h), allowing them to produce bright and stable chemiluminescence in aqueous solution for hours. As further shown, the probes disclosed allow direct detection of as little as 15,000 Mtb cells using simple and inexpensive photodiode detectors that require minimal power and may therefore be powered by solar cells as well. Importantly, the probes are processed only by live Mtb and may thus be used for both diagnosis as well as monitoring of response to antibiotics.

More particularly, in one aspect, the present invention provides a compound of the formula Ia or Ib:

Ia

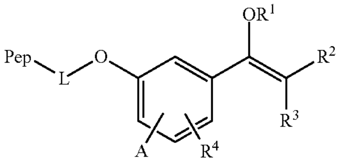

Ib

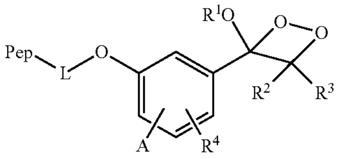

wherein $R^1$ is selected from $(C_1\text{-}C_{18})$alkyl, or $(C_3\text{-}C_7)$cycloalkyl;

$R^2$ and $R^3$ each independently is selected from a branched $(C_3\text{-}C_{18})$alkyl or $(C_3\text{-}C_7)$cycloalkyl, or $R_2$ and $R_3$ together with the carbon atom to which they are attached form a fused, spiro or bridged cyclic or polycyclic ring;

$R^4$ is H, or halogen attached either ortho or para to the —O-L-Pep group;

A is a π* acceptor group of the formula $$-(CH{=}CH)_r-E,$$

attached either ortho or para to the —O-L-Pep group, wherein r is an integer of 1 to 6, preferably 1, and E is:

(a) —CN, —COOH, or —COO$(C_1\text{-}C_{18})$alkyl optionally interrupted in the alkylene chain with one or more —O— groups and/or substituted with one or more groups each independently selected from —OH, —COOH, halogen, and —$NH_2$;

(b) a group of the formula

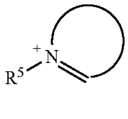 or 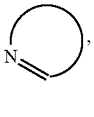, denoting a mono- or polycyclic, aromatic or nonaromatic ring system comprising the moiety

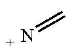 or 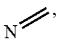, respectively, as a ring member, and linked to the alkenylene chain of group A via any atom which is a member of said mono- or polycyclic, aromatic or nonaromatic ring system, provided that a delocalized π-system extends from the nitrogen atom of

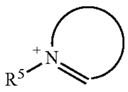
or
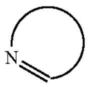

via the alkenylene chain of group A to the central aromatic ring of the compound of formula Ia or Ib, wherein said mono- or polycyclic, aromatic or nonaromatic ring system is optionally substituted with one or more groups each independently selected from halogen, —OH, —CN, —$SO_3H$ or a salt thereof, —COOH or a salt thereof, —COO—($C_1$-$C_{18}$)alkyl, ($C_1$-$C_6$)alkyl, ($C_2$-$C_6$)alkenyl, ($C_2$-$C_6$)alkynyl, a polyethylene glycol chain, and a polypropylene glycol chain, and wherein $R^5$ is H, —O—, ($C_1$-$C_8$)alkyl, ($C_2$-$C_8$)alkenyl, or ($C_2$-$C_8$)alkynyl, wherein said ($C_1$-$C_8$)alkyl, ($C_2$-$C_8$)alkenyl and ($C_2$-$C_8$)alkynyl each is optionally substituted with one or more groups each independently selected from —OH, —COOH, halogen, and —$NH_2$, and optionally interrupted with one or more —O— or —CO— groups; or (c) a group of the formula

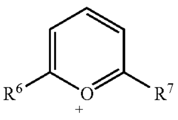

linked to the alkenylene chain of group A via a carbon atom of the pyrylium moiety, wherein $R^6$ and $R^7$ each independently is selected from H, ($C_1$-$C_6$)alkyl, ($C_2$-$C_6$)alkenyl, ($C_2$-$C_6$)alkynyl, and ($C_3$-$C_7$)cycloalkyl;

L is a linker of the formula:

L1

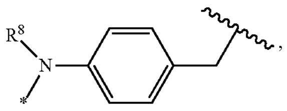

L2

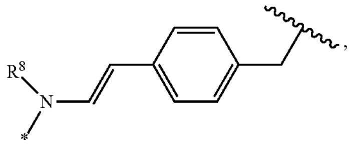

L3

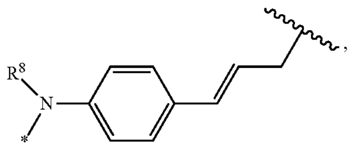

L4

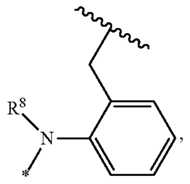

-continued

L5

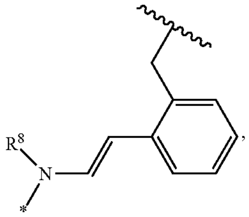

L6

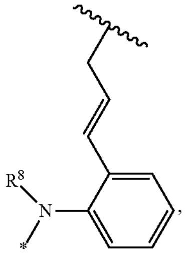

L7

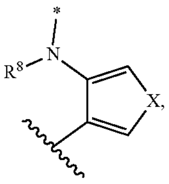

L8

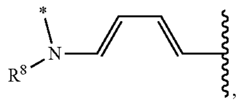
and

L9

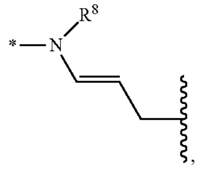

optionally substituted at the aromatic or heteroaromatic ring with one or more substituents each independently selected from ($C_1$-$C_{18}$)alkyl and ($C_3$-$C_7$)cycloalkyl, wherein X is S, O, or $NR^8$; $R^8$ each independently is H or ($C_1$-$C_{18}$)alkyl, preferably H; and the asterisk represents the point of attachment to the group Pep; and Pep is a *Mycobacterium tuberculosis* (Mtb)-specific protease cleavable peptide linked via a carboxylic group thereof, e.g., the alpha-carboxylic group thereof, and optionally acetylated at its alpha amino acid.

In particular such compounds, said Mtb-specific protease cleavable peptide is a peptide of the formula $Xaa_5$-$Xaa_4$-$Xaa_3$-$Xaa_2$-$Xaa_1$-, wherein $Xaa_1$ is an amino acid, e.g., an aliphatic amino acid such as Leu or Gln, linked via the carboxylic group thereof to group L; $Xaa_2$ is Lys; $Xaa_3$ is an amino acid, e.g., an aromatic amino acid such as 4ClPhe; $Xaa_4$ is an amino acid such as Igl, (benzyl)cysteine, or Asp; and $Xaa_5$ is either absent or represents a sequence of one or more amino acids, provided that either $Xaa_4$ or the terminal amino acid of $Xaa_5$, when present, is acetylated at its alpha amino group.

In another aspect, the present invention provides a composition comprising a dioxetane-based chemiluminescence probe as defined above, i.e., a compound of the formula Ia/Ib, and a carrier, e.g., a pharmaceutically acceptable carrier. The compounds and compositions of the invention are useful for determining the presence, or measuring the level, of Mtb-specific protease in a sample, i.e., in vitro.

In a further aspect, the present invention thus relates to a method for determining the presence, or measuring the level, of Mtb-specific protease in a sample, e.g., a biological sample such as a bodily fluid, a bodily fluid-based solution or a tissue biopsy sample, said method comprising: (i) contacting said sample with a dioxetane-based chemiluminescence probe of the formula Ia/Ib as defined above (i.e., applying said compound to said sample), wherein in the presence of Mtb-specific protease in said sample (i.e., upon exposure to Mtb-specific protease), said Mtb-specific protease cleavable peptide is cleaved from the compound of formula Ia/Ib, thereby generating an unstable phenolate-dioxetane compound, which is then decomposed through a chemiexcitation process to produce an excited intermediate that decays to its ground-state through emission of light; and (ii) imaging said sample to detect the emission of light.

In yet another aspect, the present invention relates to a method for assessing the susceptibility of Mtb present in a sample to an antibiotic drug, said method comprising: (i) contacting said sample with a dioxetane-based chemiluminescence probe of the formula Ia/Ib as defined above at a time period after contacting said sample with said antibiotic drug, wherein in the presence of Mtb-specific protease in said sample (i.e., upon exposure to Mtb-specific protease), said Mtb-specific protease cleavable peptide is cleaved from the compound of formula Ia/Ib, thereby generating an unstable phenolate-dioxetane compound, which is then decomposed through a chemiexcitation process to produce an excited intermediate that decays to its ground-state through emission of light; and (ii) imaging said sample to detect the emission of light, wherein a decrease in the intensity of emission detected in step (ii) as compared to a reference level detected after contacting a reference sample with said compound without contacting said sample with said antibiotic drug indicates that said Mtb is susceptible to said antibiotic drug.

BRIEF DESCRIPTION OF DRAWINGS

FIGS. 4A-4C show that FLASH is more sensitive to Mtb compared to common nontuberculous mycobacteria (NTM). (4A) Percent identities between Hip1 homologues found in NTM species and the Mtb sequence, and protein sequence alignments for regions surrounding the three active-site residues (Ser228, Asp463, and His490). (4B-4C) IL values for millions (4B) or thousands (4C) of cells of each species incubated with FLASH for 1 h. Error bars show standard deviation (n=3, one-way ANOVA with multiple comparisons to the no-cell control: ***, $p<0.001$).

DETAILED DESCRIPTION

Figure 1A:
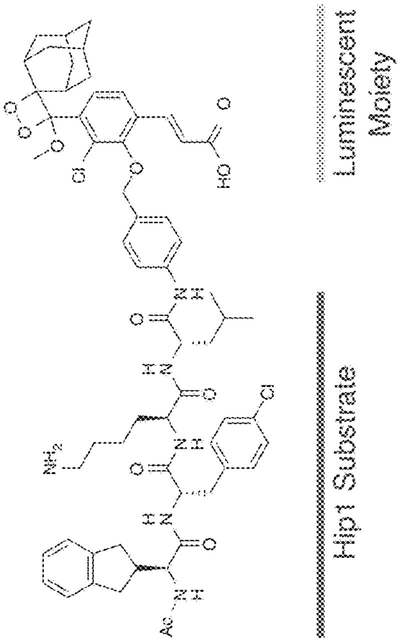
FIGS. 1A-1C show fast luminescent affordable sensor of Hip1 (FLASH). (1A) Chemical structure of the FLASH probe. (1B) FLASH comprises a peptide substrate of the Hip1 enzyme, linked to a luminescent moiety. In the presence of Hip1 enzyme expressed by Mtb, FLASH is cleaved, and the luminescent moiety produces a light signal. (1C) Proposed mechanism for light generation by the luminescent moiety
Figure 1B:
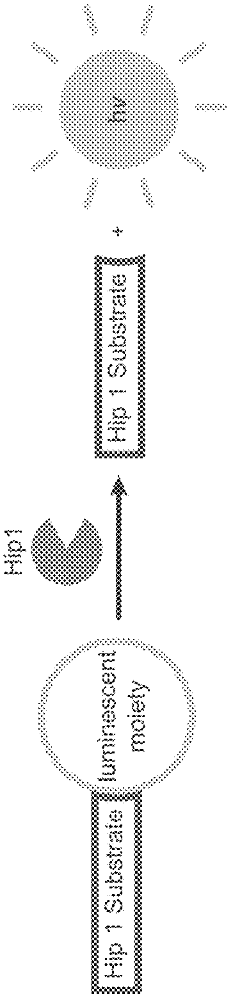
Figure 1C:
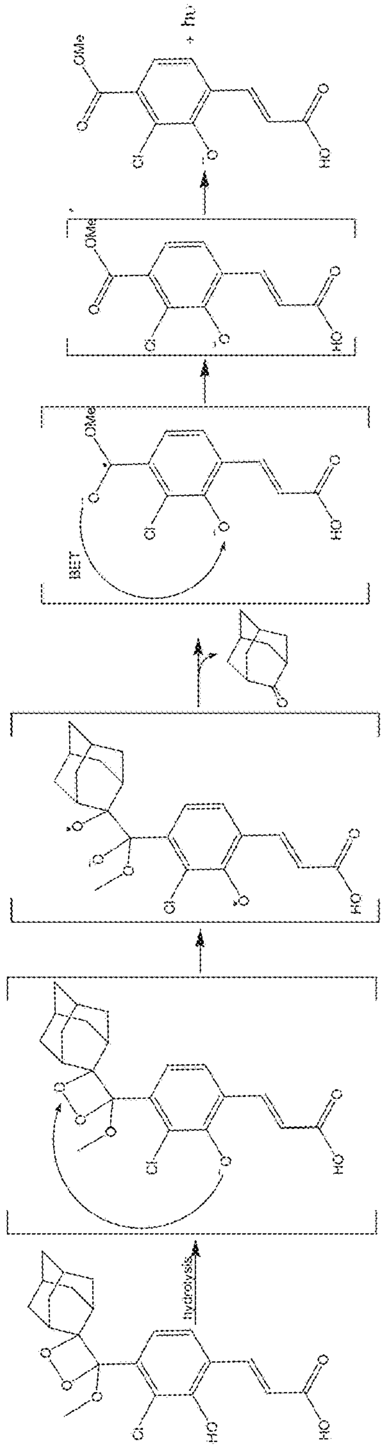

In one aspect, the present invention provides a turn-ON dioxetane-based chemiluminescence probe, more specifically a compound of the formula Ia or Ib, as defined above.

The term "alkyl" typically means a linear or branched hydrocarbyl having, e.g., 1-18 carbon atoms and includes methyl, ethyl, n-propyl, isopropyl, n-butyl, sec-butyl, isobutyl, tert-butyl, n-pentyl, isoamyl, 2,2-dimethylpropyl, n-hexyl, n-heptyl, n-octyl, n-nonyl, n-decyl, n-undecyl, n-dodecyl, n-tridecyl, n-tetradecyl, n-pentadecyl, n-hexadecyl, and the like. Preferred are ($C_1$-$C_8$)alkyl groups, more preferably ($C_1$-$C_4$)alkyl groups, most preferably methyl, ethyl, and isopropyl. The terms "alkenyl" and "alkynyl" typically mean linear or branched hydrocarbyls having, e.g., 2-8, carbon atoms and at least one double or triple bond, respectively, and include ethenyl, propenyl, 3-buten-1-yl, 2-ethenylbutyl, 3-octen-1-yl, 3-nonenyl, 3-decenyl, and the like, and propynyl, 2-butyn-1-yl, 3-pentyn-1-yl, 3-hexynyl, 3-octynyl, 4-decynyl, and the like. $C_2$-$C_6$ alkenyl and alkynyl groups are preferred, more preferably $C_2$-$C_4$ alkenyl and alkynyl.

The term "alkylene" refers to a linear or branched divalent hydrocarbon group derived after removal of hydrogen atom from an alkyl. Examples of alkylenes include, without being limited to, methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, n-tridecanylene, n-tetradecanylene, n-pentadecanylene, n-hexadecanylene, n-heptadecanylene, n-octadecanylene, n-nonadecanylene, icosanylene, henicosanylene, docosanylene, tricosanylene, tetracosanylene, pentacosanylene, and the like. The term "alkylene chain" refers to a group of the formula $—(CH_2)_n—$ derived after removal of two hydrogen atoms from a linear hydrocarbon of the formula $C_nH_{2n+2}$. The terms "alkenylene" and "alkynylene", also referred to herein as "alkenylene chain" and "alkynylene chain", denote a divalent hydrocarbon groups derived after removal of hydrogen atom from a linear alkenyl or alkynyl, respectively.

The term "cycloalkyl" means a mono- or bicyclic saturated hydrocarbyl group having, e.g., 3-7 carbon atoms such as cyclopropyl, cyclobutyl, cyclopentyl, cyclohexyl, cycloheptyl, and the like, that may be substituted, e.g., by one or more alkyl groups.

The term "halogen" as used herein refers to a halogen and includes fluoro, chloro, bromo, and iodo, but it is preferably chloro.

The term "amino acid" as used herein refers to an organic compound comprising both amine and carboxylic acid functional groups, which may be either a natural or non-natural amino acid, and occur in both L and D isomeric forms. The twenty-two amino acids naturally occurring in proteins are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of other amino acids include citrulline (Cit), diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, m-ethynyl-phenylalanine, p-chlorophenylalanine (4ClPhe), p-bromophenylalanine, p-iodophenylalanine, p-acetylphenylalanine, p-azidophenylalanine, p-propargly-oxy-phenylalanine, indanylglycine (Igl), (benzyl)cysteine, norleucine (Nle), azidonorleucine, 6-ethynyl-tryptophan, 5-ethynyl-tryptophan, 3-(6-chloroindolyl)alanine, 3-(6-bromoindolyl) alanine, 3-(5-bromoindolyl)alanine, azidohomoalanine, α-aminocaprylic acid, O-methyl-L-tyrosine, N-acetylgalactosamine-α-threonine, and N-acetylgalactosamine-α-serine.

The term "amino acid residue" as used herein refers to a residue of an amino acid after removal of hydrogen atom from an amino group thereof, e.g., its α-amino group or side chain amino group if present, and —OH group from a carboxyl group thereof, e.g., its α-carboxyl group or side chain carboxyl group if present.

The term "peptide" refers to a short chain of amino acid monomers (residues), e.g., a chain consisting of 4, 5, 6, 7, 8, 9, 10, 11, 12 or more amino acid residues, linked by peptide (amide) bonds, i.e., the covalent bond formed when a carboxyl group of one amino acid reacts with an amino group of another. The term "peptide moiety" as used herein refers to a moiety of a peptide as defined herein after removal of the hydrogen atom from a carboxylic group, i.e., either the terminal or a side chain carboxylic group, thereof, and/or a hydrogen atom from an amino group, i.e., either the terminal or a side chain amino group, thereof.

The term "peptide bond" or "amide bond" as used herein refers to the covalent bond —C(O)NH— formed between two molecules, e.g., two amino acids, when a carboxyl group of one of the molecules reacts with an amino group of the other molecule, causing the release of a water molecule.

The term "π* acceptor group" as used herein with respect to group A refers to a group containing a π* acceptor system, linked to the central aromatic ring of the compound of formula Ia or Ib via a conjugated alkenylene chain (an alkenylene chain consisting of single and double bonds alternately) and capable of accepting electrons, more specifically to a group of the formula $$—(CH{=}CH)_r—E,$$

wherein r is an integer of 1 to 6, preferably 1, and E is one of the options defined above.

In certain embodiments, the π* acceptor group A is a group of the formula $$—(CH{=}CH)_r—E,$$

wherein r is an integer of 1 to 6, preferably 1, and E is —CN, —COOH, or $—COO(C_1\text{-}C_{18})$alkyl optionally interrupted in the alkylene chain with one or more —O— groups or substituted with one or more groups each independently selected from —OH, —COOH, halogen, and $—NH_2$. Examples of such π* acceptor groups, wherein r=1, include —CH═CH—CN, —CH═CH—COOH, $—CH{=}CH—COOCH_3$, $—CH{=}CH—COOC_2H_5$, $—CH{=}CH—COOCH(CH_3)_2$, $—CH{=}CH—COOC(CH_3)_3$, and $—CH{=}CH—COO[(CH_2)_2—O]_4—CH_3$.

In other embodiments, the π* acceptor group A is a group of the formula $$—(CH{=}CH)_r—E,$$

wherein r is an integer of 1 to 6, preferably 1, and E is a group of the formula

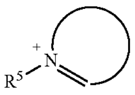 or 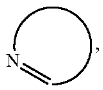, denoting a mono- or polycyclic, aromatic or nonaromatic ring system comprising the moiety

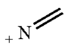 or 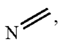, respectively, as a ring member, and linked to the alkenylene chain of group A via any atom which is a member of said mono- or polycyclic, aromatic or nonaromatic ring system, provided that a delocalized n-system extends from the nitrogen atom of

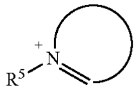 or 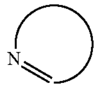

via the alkenylene chain of group A to the central aromatic ring of the compound of formula Ia or Ib, wherein said mono- or polycyclic, aromatic or nonaromatic ring system is optionally substituted with one or more groups each independently selected from halogen, —OH, —CN, —$SO_3H$ or a salt thereof, —COOH or a salt thereof, —COO—($C_1$-$C_{18}$) alkyl, ($C_1$-$C_6$)alkyl, ($C_2$-$C_6$)alkenyl, ($C_2$-$C_6$)alkynyl, a polyethylene glycol chain, and a polypropylene glycol chain; and wherein $R^5$ is H, —O—, ($C_1$-$C_8$)alkyl, ($C_2$-$C_8$)alkenyl, or ($C_2$-$C_8$)alkynyl, wherein said ($C_1$-$C_8$)alkyl, ($C_2$-$C_8$)alkenyl and ($C_2$-$C_8$)alkynyl each is optionally substituted with one or more groups each independently selected from —OH, —COOH, halogen, and —$NH_2$, and optionally interrupted with one or more —O— or —CO— groups. Preferred such π* acceptor groups are those wherein $R^5$, when present, is H, —O—, —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —CH=$CH_2$, —CH=$CHCH_3$, —$CH_2CH$=$CH_3$, or ($C_4$-$C_8$)alkenyl.

Examples of such π* acceptor groups, wherein r=1, include the groups shown in Table 1, optionally substituted at one or more of the carbon atoms of the aromatic or nonaromatic ring system with one or more groups each independently selected from halogen, —OH, —CN, —$SO_3H$ or a salt thereof, —COOH or a salt thereof, —COO—($C_1$-$C_{18}$)alkyl, ($C_1$-$C_6$)alkyl, ($C_2$-$C_6$)alkenyl, ($C_2$-$C_6$)alkynyl, a polyethylene glycol chain, and a polypropylene glycol chain, wherein $R^5$ is H, —O—, or ($C_1$-$C_8$)alkyl optionally substituted with one or more groups each independently selected from —OH, —COOH, halogen, and —$NH_2$, and optionally interrupted with one or more —O— or —CO— groups.

TABLE 1

| Certain π* acceptor groups A of the formula —CH=CH—E referred to herein |
|---|
| 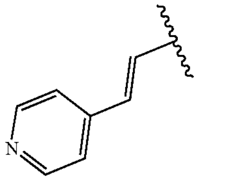 [SMILES: */C=C/c1ccncc1] |
| 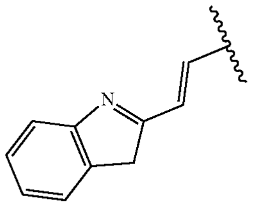 [SMILES: */C=C/C1=Nc2ccccc2C1] |
| 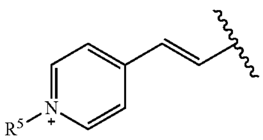 |
| 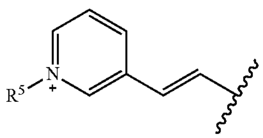 |

TABLE 1-continued

| Certain π* acceptor groups A of the formula —CH=CH—E referred to herein |
|---|
| 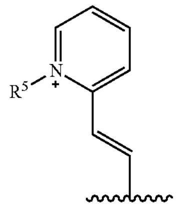 |
| 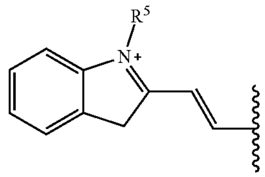 |
| 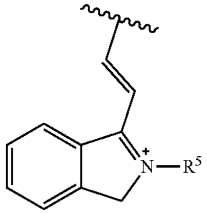 |
| 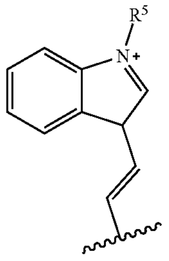 |
| 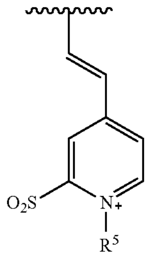 |
| 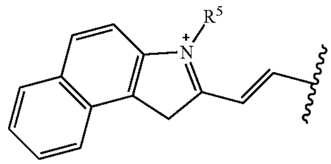 |

TABLE 1-continued
| Certain π* acceptor groups A of the formula —CH═CH—E referred to herein |
|---|
| 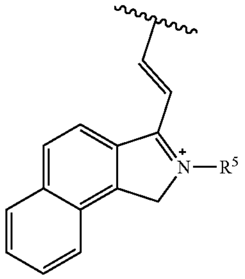 |
| 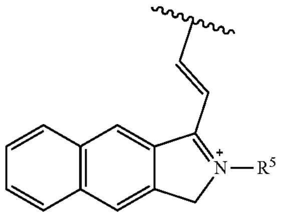 |
| 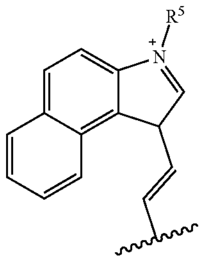 |
| 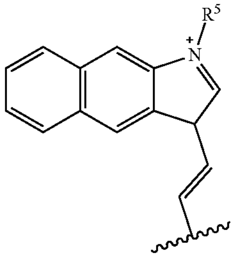 |
| 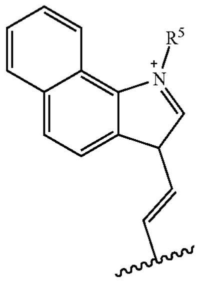 |
| 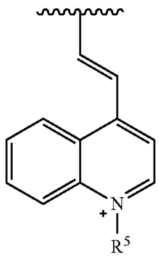 |
TABLE 1-continued
| Certain π* acceptor groups A of the formula —CH═CH—E referred to herein |
|---|
| 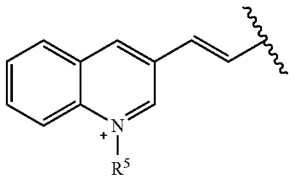 |
| 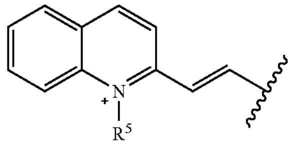 |
| 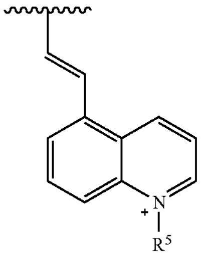 |
| 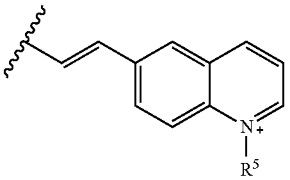 |
| 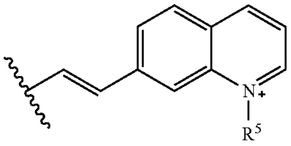 |
| 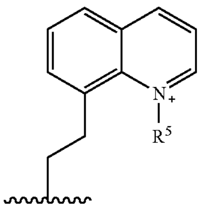 |
| 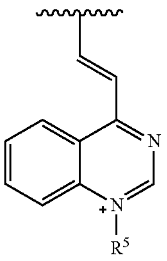 |

TABLE 1-continued
Certain π* acceptor groups A of the formula —CH═CH—E referred to herein
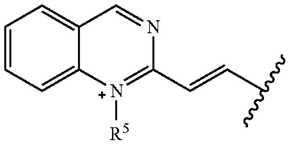
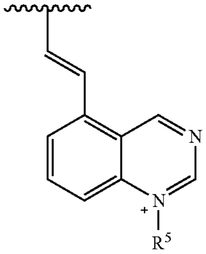
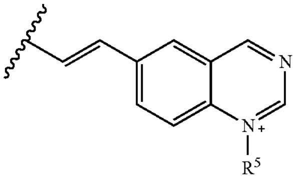
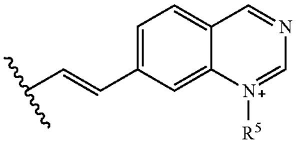
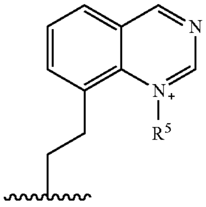
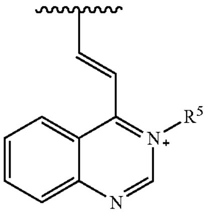
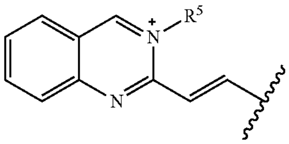
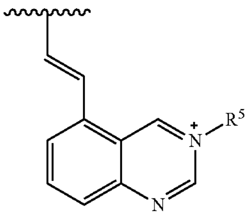
TABLE 1-continued
Certain π* acceptor groups A of the formula —CH═CH—E referred to herein
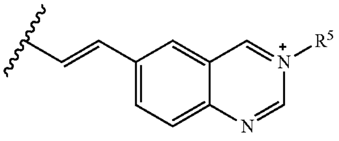
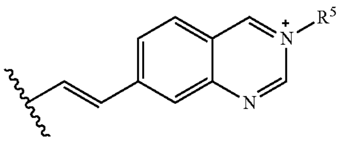
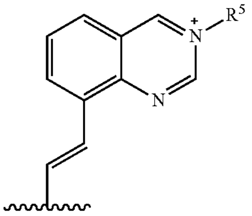
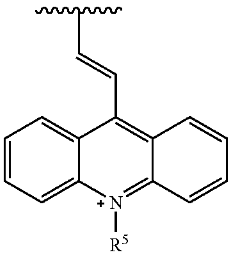
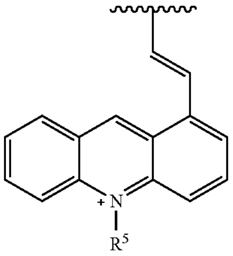
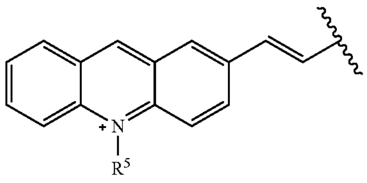
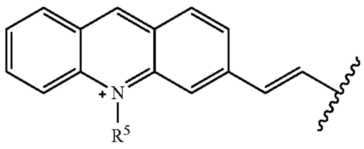

TABLE 1-continued

| Certain π* acceptor groups A of the formula —CH═CH—E referred to herein |
|---|
| 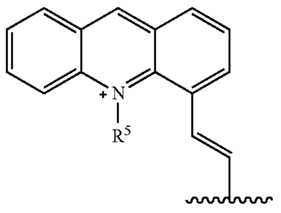 |
| 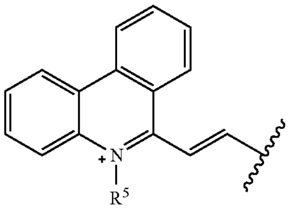 |
| 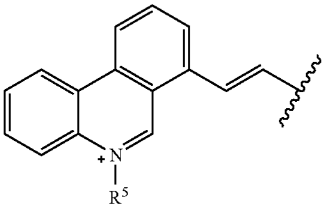 |
| 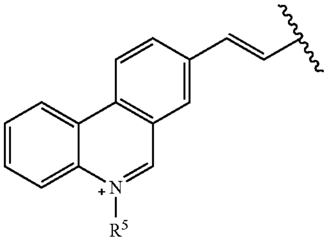 |
| 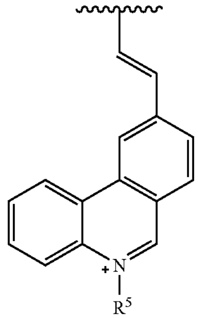 |
| 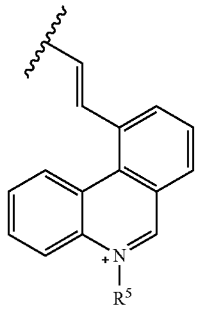 |

TABLE 1-continued

| Certain π* acceptor groups A of the formula —CH═CH—E referred to herein |
|---|
| 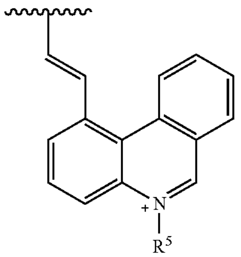 |
| 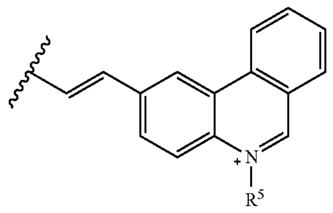 |
| 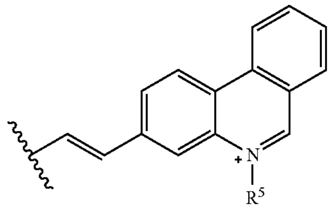 |
| 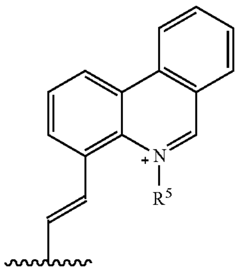 |

In further embodiments, the π* acceptor group A is a group of the formula $$-\!\!(CH{=}CH)_r\!\!-E,$$

wherein r is an integer of 1 to 6, preferably 1, and E is a group of the formula

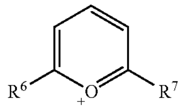

linked to the alkenylene chain of group A via a carbon atom of the pyrylium moiety, wherein $R^6$ and $R^7$ each independently is selected from H, $(C_1$-$C_6)$alkyl, $(C_2$-$C_6)$alkenyl, $(C_2$-$C_6)$alkynyl, and $(C_3$-$C_7)$cycloalkyl. Preferred such π* acceptor groups are those wherein $R^6$ and $R^7$ each independently is methyl, ethyl, propyl, isopropyl, butyl, sec-butyl, or tert-butyl. An example of such π* acceptor groups, wherein r=1, is the group shown in Table 2, which is optionally substituted at one or more of the carbon atoms of the aromatic ring system with one or more groups each independently selected from halogen, —OH, —CN, —$SO_3H$ or a salt thereof, —COOH or a salt thereof, —COO—($C_1$-$C_{18}$) alkyl, ($C_1$-$C_6$)alkyl, ($C_2$-$C_6$)alkenyl, ($C_2$-$C_6$)alkynyl, a polyethylene glycol chain, and a polypropylene glycol chain.

TABLE 2

| π* acceptor group A of the formula —CH═CH—E referred to herein |
|---|
| 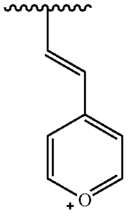 [SMILES: */C=C/c1cc[o+]cc1] |

In certain embodiments, the invention provides a compound of the formula Ia or Ib, wherein $R^1$ is a linear or branched ($C_1$-$C_8$)alkyl, preferably ($C_1$-$C_4$)alkyl, more preferably methyl, ethyl, or isopropyl.

In certain embodiments, the invention provides a compound of the formula Ia or Ib, wherein $R^2$ and $R^3$ each independently is a branched ($C_3$-$C_{18}$)alkyl or ($C_3$-$C_7$)cycloalkyl. In other embodiments, $R^2$ and $R^3$ together with the carbon atom to which they are attached form a fused, spiro or bridged polycyclic ring. In a particular such embodiment, $R^2$ and $R^3$ together with the carbon atom to which they are attached form adamantyl.

In certain embodiments, the invention provides a compound of the formula Ia or Ib, wherein $R^4$ is halogen, e.g., Cl or F, attached ortho or para, but preferably ortho, to the —O-L-Pep group.

In certain embodiments, the invention provides a compound of the formula Ia or Ib, wherein A is a π* acceptor group as defined above, more particularly wherein r=1, attached either ortho or para, preferably ortho, to the —O-L-Pep group and selected from —CH═CH—CN; —CH═CH—COOH; —CH═CH—COO($C_1$-$C_{18}$)alkyl optionally interrupted in the alkylene chain with one or more —O— groups; and the groups shown in Table 1 and Table 2, optionally substituted at one or more of the carbon atoms of the aromatic or nonaromatic ring system with one or more groups each independently selected from halogen, —OH, —CN, —$SO_3H$ or a salt thereof, —COOH or a salt thereof, —COO—($C_1$-$C_{18}$)alkyl, ($C_1$-$C_6$)alkyl, ($C_2$-$C_6$)alkenyl, ($C_2$-$C_6$)alkynyl, a polyethylene glycol chain, and a polypropylene glycol chain, wherein $R^5$ is H, —O—, or ($C_1$-$C_8$)alkyl optionally substituted with one or more groups each independently selected from —OH, —COOH, halogen, and —$NH_2$, and optionally interrupted with one or more —O— or —CO— groups.

In particular such embodiments, A is selected from —CH═CH—CN; —CH═CH—COOH; —CH═CH—COO($C_1$-$C_{18}$)alkyl optionally interrupted in the alkylene chain with one or more —O— groups; and the groups shown in Table 3, wherein $R^5$ is H, —O—, methyl, or ($C_1$-$C_8$)alkyl substituted with —COOH; $R^6$ and $R^7$ each independently is selected from ($C_1$-$C_6$)alkyl; and when the respective position is available for substitution, the aromatic ring is optionally substituted with one or two —COO— or —$SO_3$— groups in ortho position to the positively charged nitrogen atom. More particular such embodiments are those wherein A is selected from —CH═CH—CN; —CH═CH—COOH; and —CH═CH—COO($C_1$-$C_{18}$)alkyl optionally interrupted in the alkylene chain with one or more —O— groups, e.g., —$COOCH_3$, —$COOC_2H_5$, —$COO(CH_2)_2CH_3$, —$COOCH(CH_3)_2$, —$COOC(CH_3)_3$, and —$COO[(CH_2)_2$—$O]_4$—$CH_3$.

TABLE 3

| Particular π* acceptor groups A of the formula —CH═CH—E referred to herein |
|---|
| 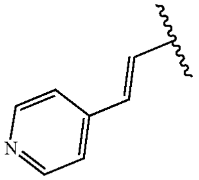 [SMILES: */C=C/c1ccncc1] |
| 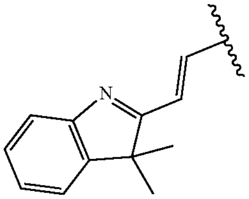 [SMILES: */C=C/C1=Nc2ccccc2C1(C)C] |
| 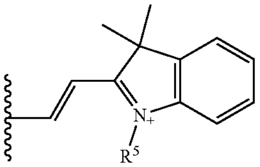 |
| 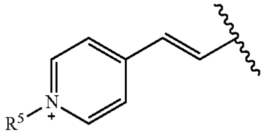 |
| 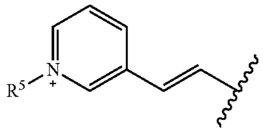 |
| 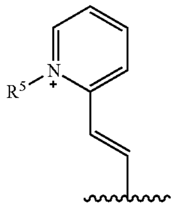 |
| 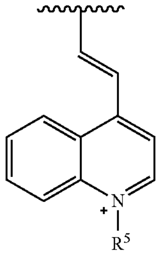 |

TABLE 3-continued

| Particular π* acceptor groups A of the formula —CH═CH—E referred to herein |
| --- |
| 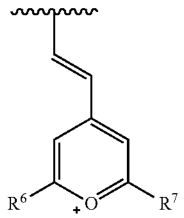 |

In certain embodiments, the invention provides a compound of the formula Ia or Ib, wherein L is a linker of the formula L1, L2 or L3, optionally substituted at the aromatic ring with one or more substituents each independently selected from $(C_1-C_{18})$alkyl and $(C_3-C_7)$cycloalkyl, wherein $R^8$ each independently is H or $(C_1-C_{18})$alkyl, preferably H. In particular such embodiments, L is a linker of the formula L1, L2 or L3, wherein $R^8$ is H, more particularly the linker of the formula L1.

In certain embodiments, the invention provides a compound of the formula Ia or Ib, wherein $R^1$ is a linear or branched $(C_1-C_8)$alkyl, preferably $(C_1-C_4)$alkyl, more preferably methyl, ethyl, or isopropyl; $R^2$ and $R^3$ together with the carbon atom to which they are attached form a fused, spiro or bridged polycyclic ring; $R^4$ is halogen, preferably chlorine, attached ortho or para, preferably ortho, to the —O-L-Pep $R^4$ group; A is a π* acceptor group as defined above wherein r=1, attached either ortho or para, preferably ortho, to the —O-L-Pep group and selected from —CH═CH—CN; —CH═CH—COOH; —CH═CH—COO$(C_1-C_{18})$alkyl optionally interrupted in the alkylene chain with one or more —O— groups; and the groups shown in Tables 1-2, optionally substituted at one or more of the carbon atoms of the aromatic or nonaromatic ring system with one or more groups each independently selected from halogen, —OH, —CN, —$SO_3H$ or a salt thereof, —COOH or a salt thereof, —COO—$(C_1-C_{18})$alkyl, $(C_1-C_6)$alkyl, $(C_2-C_6)$alkenyl, $(C_2-C_6)$alkynyl, a polyethylene glycol chain, and a polypropylene glycol chain, wherein $R^5$ is H, —O—, or $(C_1-C_8)$alkyl optionally substituted with one or more groups each independently selected from —OH, —COOH, halogen, and —$NH_2$, and optionally interrupted with one or more —O— or —CO— groups; and L is a linker of the formula L1, L2 or L3, preferably L1, optionally substituted at the aromatic ring with one or more substituents each independently selected from $(C_1-C_{18})$alkyl and $(C_3-C_7)$cycloalkyl, wherein $R^8$ each independently is H or $(C_1-C_{18})$ alkyl, preferably H. Particular such embodiments are those wherein A is selected from —CH═CH—CN; —CH═CH—COOH; —CH═CH—COO$(C_1-C_{18})$alkyl optionally interrupted in the alkylene chain with one or more —O— groups; and the groups shown in Table 3, wherein $R^5$ is H, —O—, methyl, or $(C_1-C_8)$alkyl substituted with —COOH; $R^6$ and $R^7$ each independently is selected from $(C_1-C_6)$alkyl; and when the respective position is available for substitution, the aromatic ring is optionally substituted with one or two —COO— or —$SO_3$— groups in ortho position to the positively charged nitrogen atom.

In particular embodiments, the invention provides a compound of the formula Ia or Ib as defined hereinabove, wherein $R^1$ is methyl; $R^2$ and $R^3$ together with the carbon atom to which they are attached form adamantyl; $R^4$ is halogen, preferably chlorine, attached ortho to the —O-L-Pep group; A is a π* acceptor group attached ortho to the —O-L-Pep group and selected from —CH═CH—CN; —CH═CH—COOH; and —CH═CH—COO$(C_1-C^{18})$alkyl optionally interrupted in the alkylene chain with one or more —O— groups, e.g., —$COOCH_3$, —$COOC_2H_5$, —$COO(CH_2)_2CH_3$, —$COOCH(CH_3)_2$, —$COOC(CH_3)_3$, and —COO[$(CH_2)_2$—O]$_4$—$CH_3$; and L is a linker of the formula L1, L2 or L3, preferably L1, wherein $R^8$ is H. More particular such embodiments are those wherein A is —CH═CH—CN, —CH═CH—COOH, —CH═CH—$COOCH_3$, —CH═CH—$COOC(CH_3)_3$, or —CH═CH—COO[$(CH_2)_2$—O]$_4$—$CH_3$, i.e., acrylonitrile, acrylic acid, methylacrylate, tert-butyl acrylate, or 2-(2-(2-(2-methoxyethoxy)ethoxy)ethoxy)ethyl acrylate substituent, respectively.

The chemiluminescence probe of the present invention, according to any one of the embodiments above, comprises a Mtb-specific protease cleavable peptide (group "Pep" in the formula Ia/Ib), i.e., an amino acid sequence that is cleavable by the enzyme encoded by Mtb and capable of performing proteolysis (protein catabolism) by hydrolysis of peptide bonds, wherein removal of said cleavable peptide generates an unstable phenolate-dioxetane species that decomposes through a chemiexcitation process to produce the excited intermediate, which then decays to its ground-state through emission of light.

In certain embodiments, the Mtb-specific protease cleavable peptide is a peptide of the formula $Xaa_5$-$Xaa_4$-$Xaa_3$-$Xaa_2$-$Xaa_1$-, wherein $Xaa_1$ is an amino acid linked via the carboxylic group thereof to group L; $Xaa_2$ is Lys; $Xaa_3$ is an amino acid; $Xaa_4$ is an amino acid, e.g., a non-natural amino acid; and $Xaa_5$ is either absent or represents a sequence of one or more amino acids, provided that either $Xaa_4$ or the terminal amino acid of $Xaa_5$, when present, is acetylated at its alpha amino group. In particular such embodiments, $Xaa_1$ is an aliphatic amino acid; and $Xaa_3$ is an aromatic amino acid, e.g., a non-natural aromatic amino acid. In more particular such embodiments, $Xaa_1$ is Leu or Gln; $Xaa_2$ is Lys; $Xaa_3$ is 4ClPhe; and $Xaa_4$ is Igl, (benzyl)cysteine, or Asp, i.e., Pep is a peptide of the sequence $Xaa_5$-Igl-4ClPhe-Lys-Leu-, $Xaa_5$-(benzyl)cysteine-4ClPhe-Lys-Leu-, $Xaa_5$-Asp-4ClPhe-Lys-Leu-, $Xaa_5$-Igl-4ClPhe-Lys-Gln-, $Xaa_5$-(benzyl)cysteine-4ClPhe-Lys-Gln-, or $Xaa_5$-Asp-4ClPhe-Lys-Gln-, e.g., wherein $Xaa_5$ is absent and $Xaa_4$ is thus acetylated.

In particular embodiments, disclosed herein is a compound of the formula Ia or Ib, wherein $R^1$ is a linear or branched $(C_1-C_8)$alkyl, preferably $(C_1-C_4)$alkyl, more preferably methyl, ethyl, or isopropyl; $R^2$ and $R^3$ together with the carbon atom to which they are attached form a fused, spiro or bridged polycyclic ring; $R^4$ is halogen, preferably chlorine, attached ortho or para, preferably ortho, to the —O-L-Pep $R^4$ group; A is a π* acceptor group as defined above wherein r=1, attached either ortho or para, preferably ortho, to the —O-L-Pep group and selected from —CH═CH—CN; —CH═CH—COOH; —CH═CH—COO$(C_1-C_{18})$alkyl optionally interrupted in the alkylene chain with one or more —O— groups; and the groups shown in Tables 1-2, optionally substituted at one or more of the carbon atoms of the aromatic or nonaromatic ring system with one or more groups each independently selected from halogen, —OH, —CN, —$SO_3H$ or a salt thereof, —COOH or a salt thereof, —COO—$(C_1-C_{18})$alkyl, $(C_1-C_6)$alkyl, $(C_2-C_6)$alkenyl, $(C_2-C_6)$alkynyl, a polyethylene glycol chain, and a polypropylene glycol chain, wherein $R^5$ is H, —O—, or $(C_1-C_8)$alkyl optionally substituted with one or more groups each independently selected from —OH, —COOH, halogen, and —$NH_2$, and optionally interrupted with one or more —O— or —CO— groups; and L is a linker of the formula L1, L2 or L3, preferably L1, optionally substituted at the aromatic ring with one or more substituents each independently selected from ($C_1$-$C_{18}$)alkyl and ($C_3$-$C_7$)cycloalkyl, wherein $R^8$ each independently is H or ($C_1$-$C_{18}$) alkyl, preferably H; and Pep is a peptide of the sequence $Xaa_5$-$Xaa_4$-$Xaa_3$-$Xaa_2$-$Xaa_1$-, wherein $Xaa_1$ is Leu; $Xaa_2$ is Lys; $Xaa_3$ is 4ClPhe; $Xaa_4$ is acetylated Igl; and $Xaa_5$ is absent. Particular such embodiments are those wherein A is selected from —CH═CH—CN; —CH═CH—COOH; —CH═CH—COO($C_1$-$C_{18}$)alkyl optionally interrupted in the alkylene chain with one or more —O— groups; and the groups shown in Table 3, wherein $R^5$ is H, —O—, methyl, or ($C_1$-$C_8$)alkyl substituted with —COOH; $R^6$ and $R^7$ each independently is selected from ($C_1$-$C_6$)alkyl; and when the respective position is available for substitution, the aromatic ring is optionally substituted with one or two —COO— or —$SO_3$— groups in ortho position to the positively charged nitrogen atom.

In specific such embodiments, disclosed herein is a compound of the formula Ia or Ib, wherein $R^1$ is methyl; $R^2$ and $R^3$ together with the carbon atom to which they are attached form adamantyl; $R^4$ is Cl attached ortho to the —O-L-Pep group; A is a π* acceptor group attached ortho to the —O-L-Pep group and selected from —CH═CH—CN, —CH═CH—COOH, —CH═CH—$COOCH_3$, —CH═CH—$COOC(CH_3)_3$, or —CH═CH—$COO[(CH_2)_2$—$O]_4$—$CH_3$; L is a linker of the formula L1, L2 or L3, preferably L1, wherein $R^8$ is H; and Pep is a peptide of the sequence $Xaa_5$-$Xaa_4$-$Xaa_3$-$Xaa_2$-$Xaa_1$-, wherein $Xaa_1$ is Leu; $Xaa_2$ is Lys; $Xaa_3$ is 4ClPhe; $Xaa_4$ is acetylated Igl; and $Xaa_5$ is absent, e.g., the compounds herein identified Ib-1a, Ib-1b (MTCL; FLASH), Ib-1c, Ib-1d, and Ib-1e, respectively (Table 4).

TABLE 4

Specific compounds of the formula Ia/Ib disclosed herein

Ib-1a

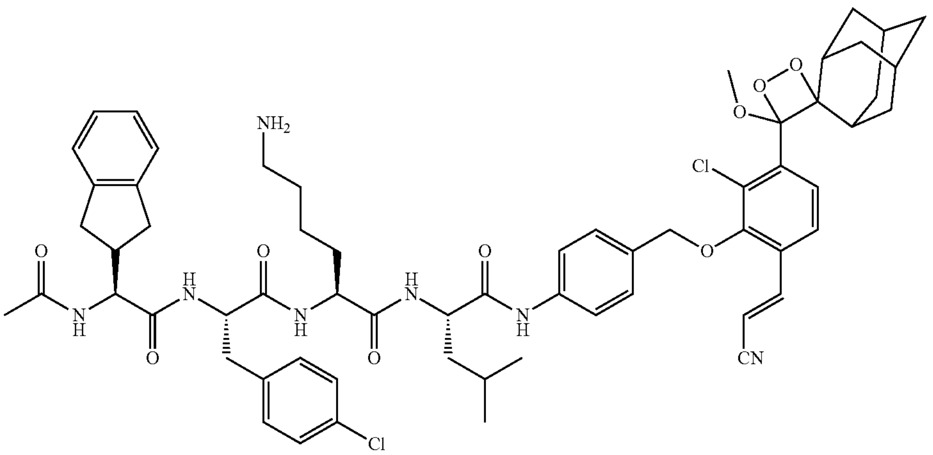 [SMILES: COC1(c2ccc(/C=C/C#N)c(OCc3ccc(NC(=O)[C@H](CC(C)C)NC(=O)[C@H](CCCCN)NC(=O)[C@H](Cc4ccc(Cl)cc4)NC(=O)[C@@H](NC(C)=O)C4Cc5ccccc5C4)cc3)c2Cl)OOC12C1CC3CC(C1)CC2C3]

Ib-1b (MTCL)

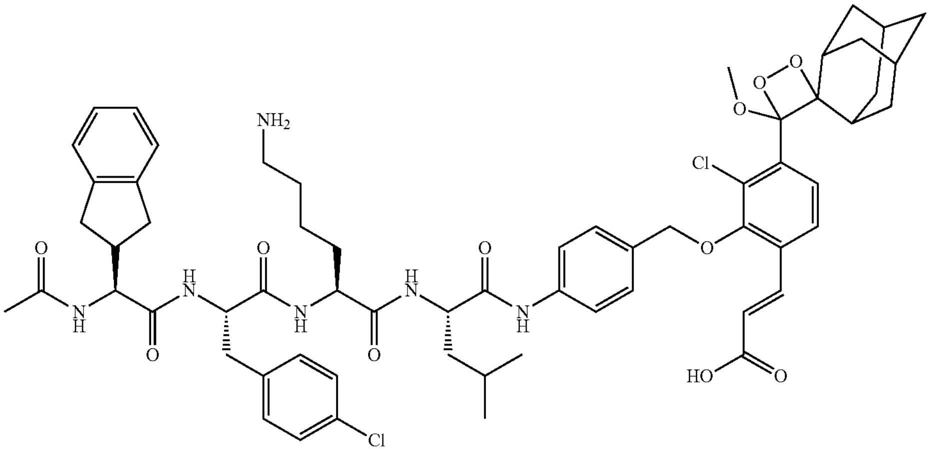 [SMILES: COC1(c2ccc(/C=C/C(=O)O)c(OCc3ccc(NC(=O)[C@H](CC(C)C)NC(=O)[C@H](CCCCN)NC(=O)[C@H](Cc4ccc(Cl)cc4)NC(=O)[C@@H](NC(C)=O)C4Cc5ccccc5C4)cc3)c2Cl)OOC12C1CC3CC(C1)CC2C3]

TABLE 4-continued
| Specific compounds of the formula Ia/Ib disclosed herein | |
|---|---|
| Ib-1c | 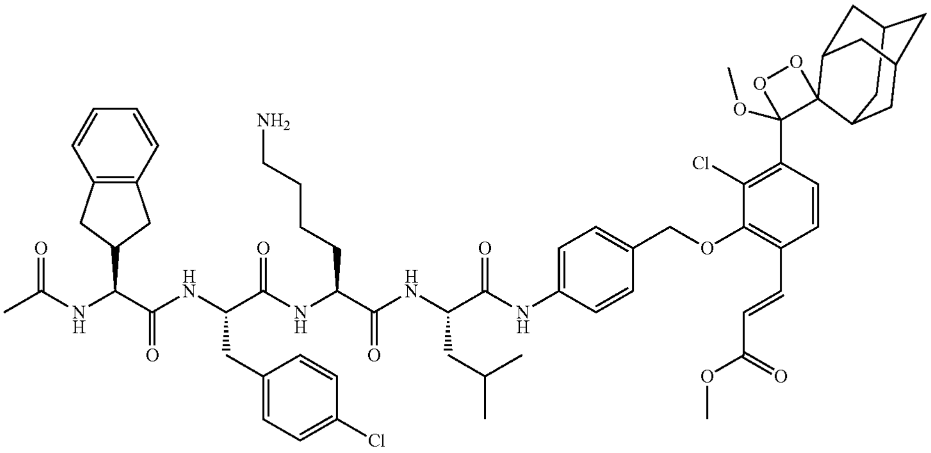 [SMILES: COC(=O)/C=C/c1ccc(C2(OC)OOC23C2CC4CC(C2)CC3C4)c(Cl)c1OCc1ccc(NC(=O)[C@H](CC(C)C)NC(=O)[C@H](CCCCN)NC(=O)[C@H](Cc2ccc(Cl)cc2)NC(=O)[C@@H](NC(C)=O)C2Cc3ccccc3C2)cc1] |
| Ib-1d | 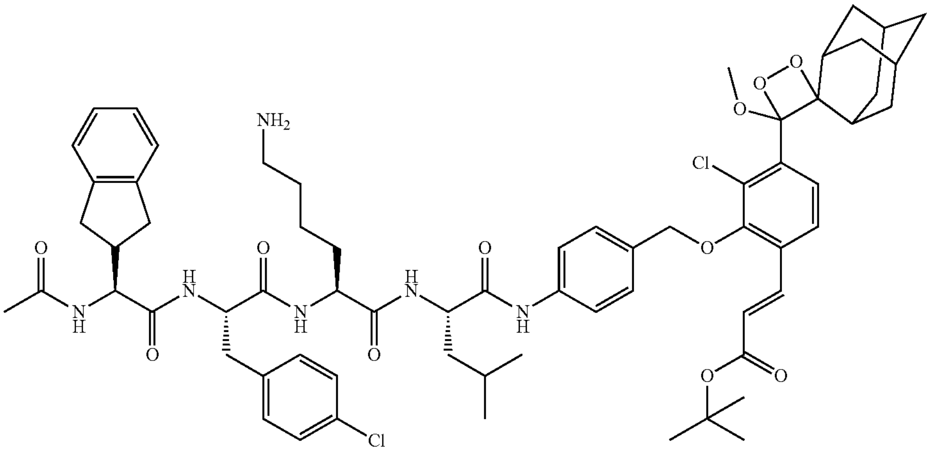 [SMILES: COC1(c2ccc(/C=C/C(=O)OC(C)(C)C)c(OCc3ccc(NC(=O)[C@H](CC(C)C)NC(=O)[C@H](CCCCN)NC(=O)[C@H](Cc4ccc(Cl)cc4)NC(=O)[C@@H](NC(C)=O)C4Cc5ccccc5C4)cc3)c2Cl)OOC12C1CC3CC(C1)CC2C3] |
| Ib-1e | 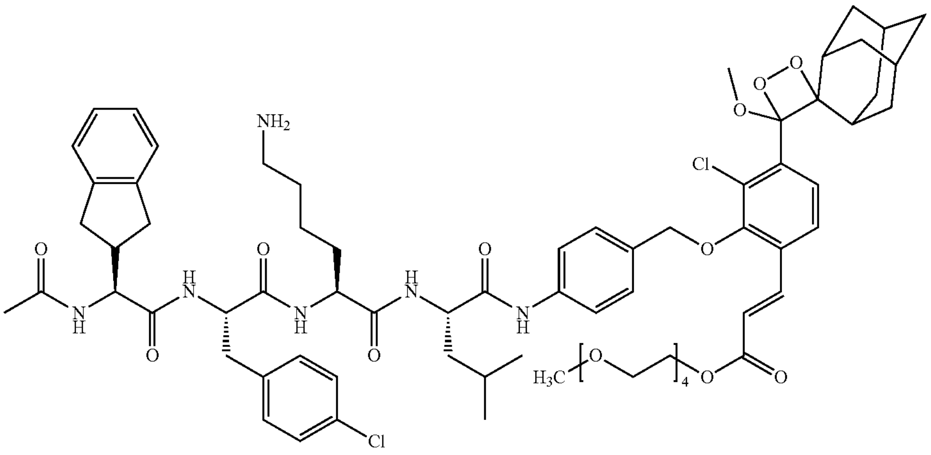 |

In another aspect, the present invention provides a composition comprising a dioxetane-based chemiluminescence probe as disclosed herein, i.e., a compound of the formula Ia/Ib as defined in any one of the embodiments above, and a carrier, e.g., a pharmaceutically acceptable carrier. Such compositions may be in a liquid, solid or semisolid form, and may further include inert ingredients, fillers, diluents, and/or excipients.

In specific embodiments, the compound comprised within the composition disclosed herein is a chemiluminescence probe of the formula Ia/Ib, wherein $R^1$ is methyl; $R^2$ and $R^3$ together with the carbon atom to which they are attached form adamantyl; $R^4$ is Cl attached ortho to the —O-L-Pep group; A is a π* acceptor group attached ortho to the —O-L-Pep group and selected from —CH═CH—CN, —CH═CH—COOH, —CH═CH—$COOCH_3$, —CH═CH—$COOC(CH_3)_3$, or —CH═CH—$COO[(CH_2)_2$—$O]_4$—$CH_3$; L is a linker of the formula L1, L2 or L3, preferably L1, wherein $R^8$ is H; and Pep is a peptide of the sequence $Xaa_5$-$Xaa_4$-$Xaa_3$-$Xaa_2$-$Xaa_1$-, wherein $Xaa_1$ is Leu; $Xaa_2$ is Lys; $Xaa_3$ is 4ClPhe; $Xaa_4$ is acetylated Igl; and $Xaa_5$ is absent, e.g., a compound selected from those listed in Table 4.

The chemiluminescence probes of the invention as well as their compositions are capable of determining the presence, or measuring the level, of Mtb-specific protease in a sample, i.e., in vitro, and are thus useful in determining the presence, or measuring the level, of Mtb in said sample. These probes therefore may be further used for assessing the susceptibility of Mtb present in a sample, i.e., in vitro, to an antibiotic drug.

In a further aspect, the present invention thus relates to a method (referred to herein as "Method A") for determining the presence, or measuring the level, of Mtb-specific protease in a sample, i.e., in vitro, said method comprising (i) contacting said sample with a dioxetane-based chemiluminescence probe of the formula Ia/Ib as defined above, wherein in the presence of Mtb-specific protease in said sample, said Mtb-specific protease cleavable peptide is cleaved from the compound of formula Ia/Ib, thereby generating an unstable phenolate-dioxetane compound, which is then decomposed through a chemiexcitation process to produce an excited intermediate that decays to its ground-state through emission of light; and (ii) imaging said sample to detect the emission of light.

In yet another aspect, the present invention relates to a method (referred to herein as "Method B") for assessing (i.e., evaluating) the susceptibility of Mtb present in a sample to an antibiotic drug, said method comprising: (i) contacting said sample with a dioxetane-based chemiluminescence probe of the formula Ia/Ib as defined above at a time period after contacting said sample with said antibiotic drug, wherein in the presence of Mtb-specific protease in said sample, said Mtb-specific protease cleavable peptide is cleaved from the compound of formula Ia/Ib, thereby generating an unstable phenolate-dioxetane compound, which is then decomposed through a chemiexcitation process to produce an excited intermediate that decays to its ground-state through emission of light; and (ii) imaging said sample to detect the emission of light, wherein a decrease in the intensity of emission detected in step (ii) as compared to a reference level detected after contacting said sample with said compound without contacting said sample with said antibiotic drug indicates that said Mtb is susceptibility to said antibiotic drug.

The sample analyzed according to the methods disclosed herein may be any sample, e.g., a biological sample. The term "biological sample" as used herein refers to a tissue biopsy sample; a bodily fluid such as an amniotic fluid, aqueous humour, vitreous humour, bile, blood serum, breast milk, cerebrospinal fluid (CSF), pleural fluid, cerumen (earwax), endolymph, perilymph, female ejaculate, gastric juice, mucus, peritoneal fluid, saliva, sebum (skin oil), semen, sweat, tears, vaginal secretion, vomit, urine, or pus; or a bodily fluid-based solution, i.e., an aqueous solution in which a bodily fluid is dissolved.

In particular embodiments, Method A is aimed at diagnosing whether a subject is infected with Mtb, i.e., suffering from pulmonary tuberculosis, and the sample treated according to said method is a biological sample obtained from said subject, more particularly a bodily fluid such as sputum (a coughed-up material from the lower airways, i.e., trachea and bronchi), pleural fluid (a fluid found between the layers of the pleura), or CSF (a body fluid found in the brain and spinal cord); or a biopsied tissue. In other embodiments, Method B is aimed at assessing the susceptibility of Mtb obtained from a subject suffering from pulmonary tuberculosis to an antibiotic drug, or for monitoring the response of said Mtb to an antibiotic treatment, and the sample treated according to said method is a biological sample as defined above.

The term "subject" as used herein refers to any mammal, e.g., a human, non-human primate, horse, ferret, dog, cat, cow, and goat. In a preferred embodiment, the term "subject" denotes a human, i.e., an individual.

In specific embodiments, the compound applied to said sample, according to each one of the methods disclosed herein, is a chemiluminescence probe of the formula Ia/Ib, wherein $R^1$ is methyl; $R^2$ and $R^3$ together with the carbon atom to which they are attached form adamantyl; $R^4$ is Cl attached ortho to the —O-L-Pep group; A is a π* acceptor group attached ortho to the —O-L-Pep group and selected from —CH═CH—CN, —CH═CH—COOH, —CH═CH—$COOCH_3$, —CH═CH—$COOC(CH_3)_3$, or —CH═CH—$COO[(CH_2)_2$—$O]_4$—$CH_3$; L is a linker of the formula L1, L2 or L3, preferably L1, wherein $R^8$ is H; and Pep is a peptide of the sequence $Xaa_5$-$Xaa_4$-$Xaa_3$-$Xaa_2$-$Xaa_1$-, wherein $Xaa_1$ is Leu; $Xaa_2$ is Lys; $Xaa_3$ is 4ClPhe; $Xaa_4$ is acetylated Igl; and $Xaa_5$ is absent, e.g., a compound selected from those listed in Table 4.

The chemiluminescence emission of the probes of the present invention can be detected utilizing any technique or procedure known in the art.

Optical molecular imaging is a promising technique that provides a high degree of sensitivity and specificity in tumor margin detection. Furthermore, existing clinical applications have proven that optical molecular imaging is a powerful intraoperative tool for guiding surgeons performing precision procedures, thus enabling radical resection and improved survival rates. An example of a clinically approved instrument for minimally invasive surgical procedures under fluorescence guidance is the da Vinci Surgical System (Haber et al., 2010). This instrument is featured with a 3D HD vision system for a clear and magnified view inside a patient's body and allows surgeons to perform complex and routine procedures through a few small openings, similar to traditional laparoscopy. In addition, the following systems have already been applied in surgeries for breast cancer, liver metastases and bypassing graft surgery: The Hamamatsu's Photodynamic Eye (PDE™), Artemis™ and Novadaq SPY™ (Novadaq Technologies Inc., Toronto, Canada) (Chi et al., 2014). Several existing intraoperative NIR fluorescence molecular imaging systems were evaluated in clinical trials; including, Fluobeam®, FLARE™ and GXMI Navigator. They have played an important role in operation convenience, improving image assessment and increasing detection depth (Chi et al., 2014).

In recent years, there has been a great progress in the development of cameras and lasers for optical fluorescence imaging in the IR range (Mieog et al., 2011; Troyan et al., 2009). In parallel, there is a vast clinical use of low molecular weight (MW) organic dyes such as ICG and methylene blue for determining cardiac output, hepatic function and liver blood flow, and for ophthalmic angiography. In 2015, the fluorescence imaging system, Xiralite®, gained FDA approval for visualization of microcirculation in the hands (for inflammation and perfusion-related disorders).

The invention will now be illustrated by the following non-limiting Examples.

EXAMPLES

Chemistry

General Methods

All reactions requiring anhydrous conditions were performed under an argon atmosphere. All reactions were carried out at room temperature unless stated otherwise. Chemicals and solvents were either A.R. grade or purified by standard techniques. TLC: silica gel plates Merck 60 F254: compounds were visualized by irradiation with UV light. Column chromatography (FC): silica gel Merck 60 (particle size 0.040-0.063 mm), eluent given in parentheses. RP-HPLC: C18 5u, 250×4.6 mm, eluent given in parentheses. Preparative RP-HPLC: C18 5u, 250×21 mm, eluent given in parentheses. $^1$H-NMR spectra were recorded using Bruker Avance operated at 400 MHz. $^{13}$C-NMR spectra were recorded using Bruker Avance operated at 100 MHz. Chemical shifts were reported in ppm on the 8 scale relative to a residual solvent ($CDCl_3$: δ=7.26 for $^1$H-NMR and for 77.16 $^{13}$C-NMR). Mass spectra were measured on Waters Xevo TQD. Chemiluminescence was recorded on Molecular Devices Spectramax i3×. Fluorescence quantum yield was determined using Hamamatsu Quantaurus-QY. All reagents including salts and solvents were purchased from Sigma-Aldrich. Light irradiation for photochemical reactions: LED PAR38 lamp (19W, 3000K).

Synthesis of MTCL (FLASH)

MTCL was synthesized as depicted in Scheme 3.

Compound 1. As depicted in Scheme 3, step (a), to a solution of Fmoc-Leu-OH (510 mg, 1.44 mmol) and 4-aminobenzyl alcohol (200 mg, 1.62 mmol) in THF (50 mL) was added EEDQ (467 mg, 1.90 mmol), and the mixture was stirred at room temperature and monitored by TLC (Hex:EtOAc 60:40). After completion, the solvent was removed under reduced pressure and the residue was dissolved in EtOAc (100 ml) and was washed with brine (50 ml). The organic layer was separated, dried over $Na_2SO_4$ and evaporated under reduced pressure. The crude product was purified by column chromatography on silica gel (Hex:EtOAc 70:30). Compound 1 was obtained as a white solid (567 mg, 86% yield).

Compound 2. As depicted in Scheme 3, step (b), to a solution of compound 1 (500 mg, 1.09 mmol) and NaI (490 mg, 3.27 mmol) in MeCN (15 ml) was added TMSCI (415 µl, 3.27 mmol) at 0° C. The mixture was stirred at room temperature for 60 minutes and monitored by TLC (Hex:EtOAc 70:30). After full consumption of starting material, the reaction mixture diluted with EtOAc (100 ml) and was washed with brine (50 ml). The organic layer was separated, dried over $Na_2SO_4$ and evaporated under reduced pressure. The crude product was purified by column chromatography on silica gel (Hex:EtOAc 70:30). Compound 2 was obtained as a pale yellowish solid (510 mg, 83% yield).

Compound 4. As depicted in Scheme 3, step (c), phenol enol ether 3 (Hananya et al., 2019) (100 mg, 0.24 mmol) and $K_2CO_3$ (66 mg, 0.48 mmol) were dissolved in DMF (2 ml). The solution stirred for 5 minutes, before compound 2 (136 mg, 0.24 mmol) was added. The reaction mixture stirred at room temperature and monitored by TLC (Hex:EtOAc 80:20). After completion, the reaction mixture diluted with EtOAc (100 ml) and was washed with 0.1M HCl (50 ml) and brine (50 ml). The organic layer was separated, dried over $Na_2SO_4$ and evaporated under reduced pressure. The crude product was purified by column chromatography on silica gel (Hex:EtOAc 80:20). Compound 4 was obtained as a white solid (174 mg, 85% yield).

Compound 5. As depicted in Scheme 3, step (d), compound 4 (150 mg, 0.18 mmol) and piperidine (90 µl, 0.88 mmol) were dissolved in DMF (5 mL). The solution stirred for 30 minutes at room temperature and monitored by RP-HPLC (gradient of ACN in water). After full deprotection of the Fmoc was observed the solvent was removed under reduced pressure and the crude was dissolved in EtOAc was washed twice with 0.1M HCl (50 ml) and brine (50 ml). The organic layer was separated, dried over $Na_2SO_4$ and evaporated under reduced pressure. Then, the crude was added a premixed DMF (5 mL) solution containing Fmoc-Lys (alloc)-OH (83 mg, 0.18 mmol), HBTU (100 mg, 0.26 mmol) and DIPEA (65 µl, 0.36 mmol). The reaction was stirred for 60 minutes at room temperature and monitored by RP-HPLC (gradient of ACN in water). After completion, the reaction mixture diluted with EtOAc (100 ml) and was washed with 0.1M HCl (50 ml) and brine (50 ml). The organic layer was separated, dried over $Na_2SO_4$ and evaporated under reduced pressure. The crude product was purified by column chromatography on silica gel (Hex:EtOAc 50:50). Compound 5 was obtained as a white solid (140 mg, 75% yield).

Compound 6. As depicted in Scheme 3, step (e), compound 5 (140 mg, 0.13 mmol) and piperidine (65 µl, 0.66 mmol) were dissolved in DMF (5 ml). The solution stirred for 30 minutes at room temperature and monitored by RP-HPLC (gradient of MeCN in water). After full deprotection of the Fmoc was observed the solvent was removed under reduced pressure and the crude was dissolved in EtOAc was washed twice with 0.1M HCl (50 ml) and brine (50 ml). The organic layer was separated, dried over $Na_2SO_4$ and evaporated under reduced pressure. Then, the crude was added a premixed DMF (5 mL) solution containing Fmoc-4ClPhe-OH (60 mg, 0.14 mmol), HBTU (74 mg, 0.24 mmol) and DIPEA (40 µL, 0.24 mmol). The reaction was stirred for 60 minutes at room temperature and monitored by RP-HPLC (gradient of MeCN in water). After completion, the reaction mixture diluted with EtOAc (100 ml) and was washed with 0.1M HCl (50 ml) and brine (50 ml). The organic layer was separated, dried over $Na_2SO_4$ and evaporated under reduced pressure. The crude product was purified by column chromatography on silica gel (Hex:EtOAc 50:50). Compound 6 was obtained as a white solid (120 mg, 74% yield).

Compound 7. As depicted in Scheme 3, step (f), compound 6 (120 mg, 0.10 mmol) and piperidine (50 µl, 0.5 mmol) were dissolved in DMF (5 ml). The solution stirred for 30 minutes at room temperature and monitored by RP-HPLC (gradient of ACN in water). After full deprotection of the Fmoc was observed the solvent was removed under reduced pressure and the crude was dissolved in EtOAc was washed twice with 0.1M HCl (50 ml) and brine (50 ml). The organic layer was separated, dried over $Na_2SO_4$ and evaporated under reduced pressure. Then, the crude was added a premixed DMF (5 ml) solution containing Ac-Igl-OH (35 mg, 0.15 mmol), HBTU (76 mg, 0.2 mmol) and DIPEA (40 µL, 0.25 mmol). The reaction was stirred for 60 minutes at room temperature and monitored by RP-HPLC (gradient of ACN in water). Upon completion, the solvent was concentrated under reduced pressure and the product was purified by preparative RP-HPLC (gradient of ACN in water). Compound 7 was obtained as a white solid (72 mg, 61% yield).

MTCL. As depicted in Scheme 3, step (g), compound 7 (50 mg, 0.04 mmol) was dissolved in DCM (3 ml), followed by the addition of DMBA (25 mg, 0.16 mmol) and tetrakis(triphenylphosphine)palladium(5 mg, 0.004 mmol). The reaction was stirred at room temperature and monitored by RP-HPLC (gradient of ACN in water). Upon full deprotection of the allyl protecting groups, DCM (20 ml) and a catalytic amount of methylene blue were added to the mixture. Then, oxygen was bubbled through the solution while irradiating with yellow light. The reaction was monitored by RP-HPLC (gradient of ACN in water). Upon completion, 15 min, the solvent was concentrated under reduced pressure and the product was purified by preparative RP-HPLC (gradient of ACN in water). MTCL was obtained as a white solid (30 mg, 67% yield).

Schwmw 3: Synthesis of MTCL

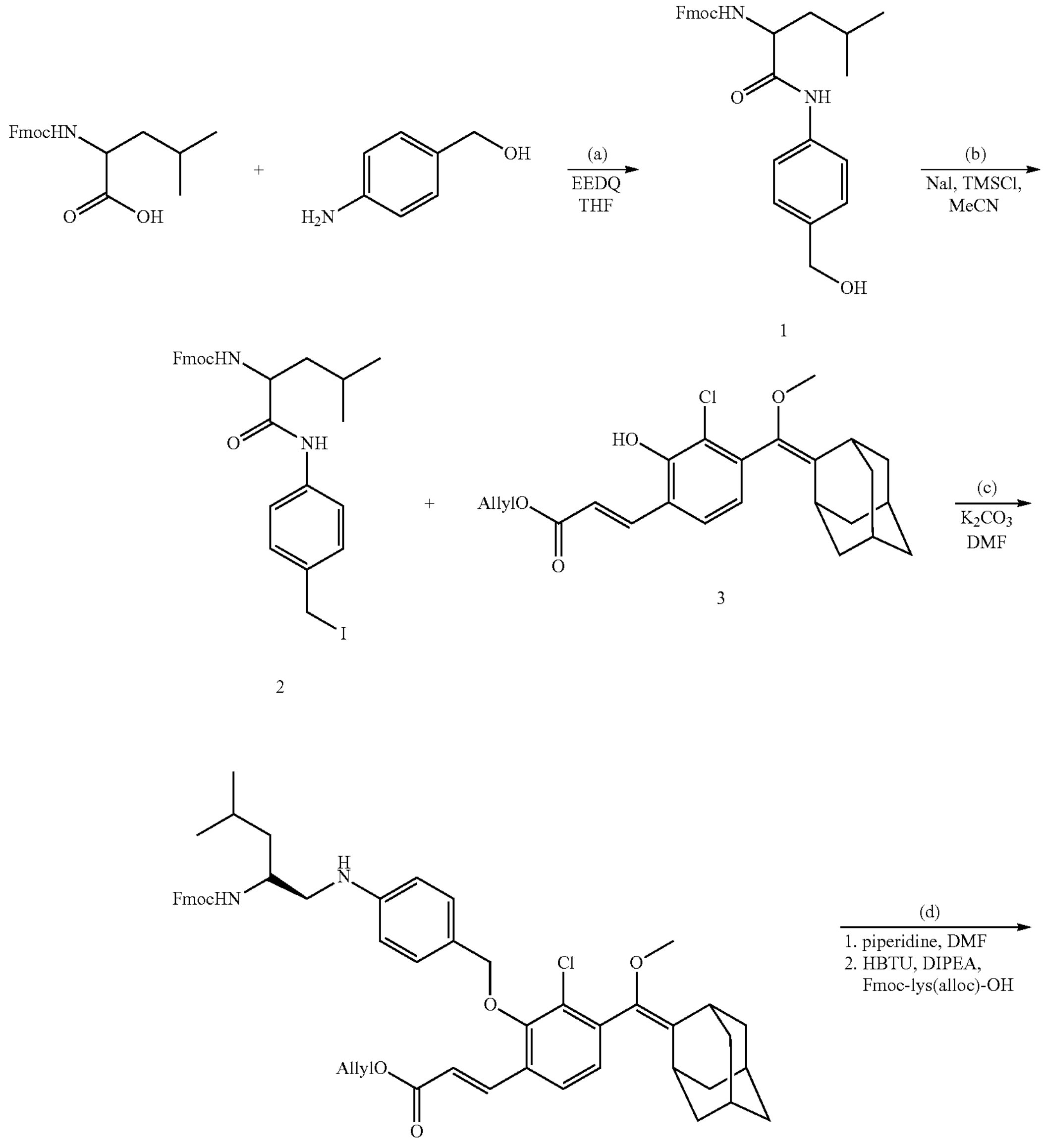

1

2

3

4

-continued
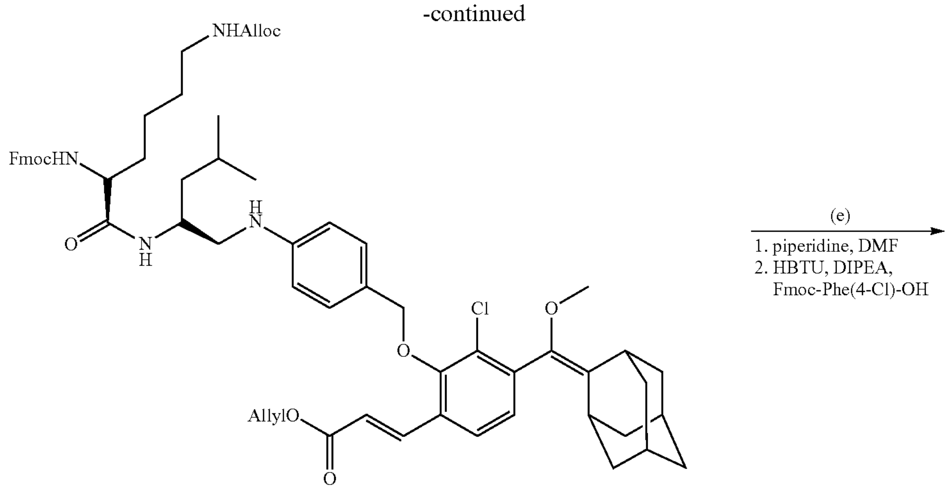
5
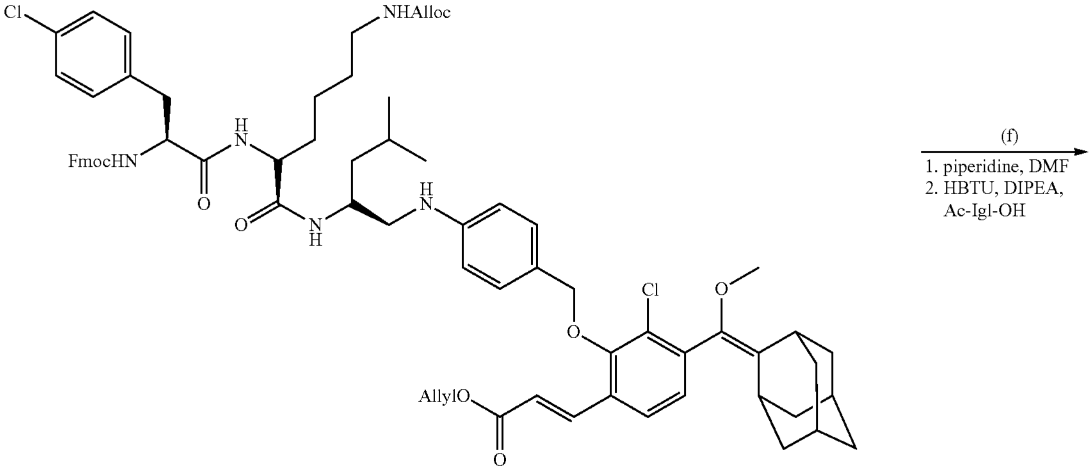
6
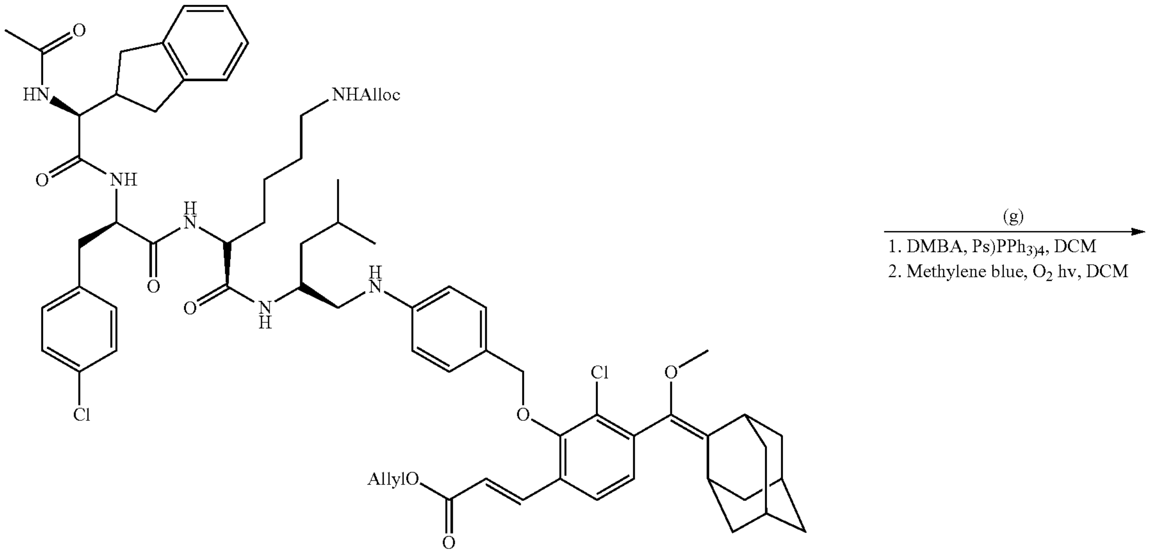
7

-continued

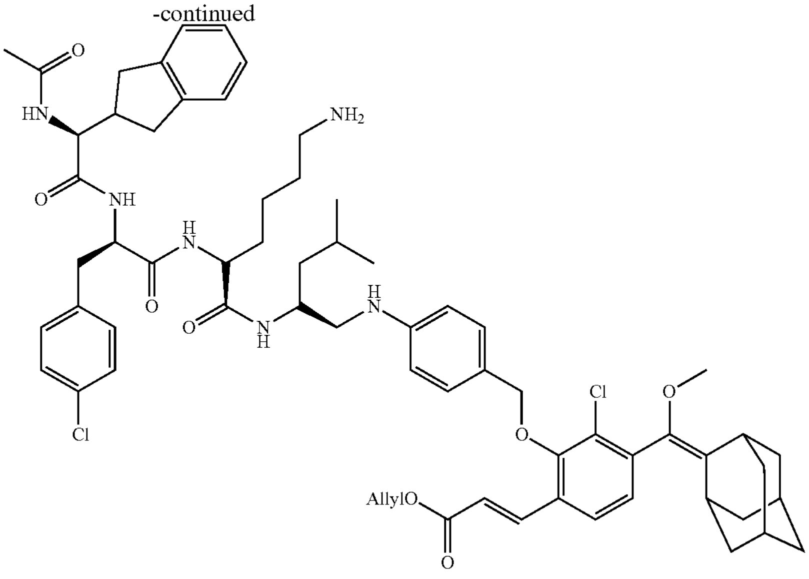

MTCL

Biology

Bacterial Culture

Clinical isolates of nontuberculous mycobacteria (NTM), more specifically, *Mycobacterium kansasii, Mycobacterium gordonae, Mycobacterium intracellulare, Mycobacterium scrofulaceum, Mycobacterium avium, Mycobacterium chelonae*, and *Mycobacterium abscessus*, were obtained from the Johns Hopkins University Center for Tuberculosis Research.

Mtb H37Rv and all nontuberculous mycobacteria were cultured in liquid Middlebrook 7H9/OADC medium (4.7 g/L 7H9 powder, 0.2% w/v glycerol, 0.05% w/v Tween-80, and 10% v/v OADC supplement) or solid Middlebrook 7H10 agar plates (19 g/L 7H10 powder, 1% w/v glycerol, 10% v/v OADC supplement). Middlebrook 7H9 powder contains 0.5 g/L ammonium sulfate, 2.5 g/L disodium sulfate, 1 g/L monopotassium sulfate, 0.1 g/L sodium citrate, 0.05 g/L magnesium sulfate, 0.5 mg/L calcium chloride, 1 mg/L zinc sulfate, 1 mg/L copper sulfate, 0.04 g/L ferric ammonium citrate, 0.5 g/L L-glutamic acid, 1 mg/L pyridoxine, and 0.5 mg/L biotin. OADC contains 8.5 g/L sodium chloride, 50 g/L bovine serum albumin fraction V, 20 g/L dextrose, 0.625 g/L oleic acid, and 0.05 g/L catalase. Middlebrook 7H10 powder contains 7H9 powder plus 0.25 mg/L malachite green and 15 g/L agar. Mtb $mc^2$6020 was cultured in liquid 7H9/OADC medium supplemented with 24 mg/L pantothenate, 80 mg/L L-lysine, and 0.2% w/v casamino acids or solid 7H9 plates (15 g agar, 4.7 g 7H9 powder, 0.1% w/v glycerol, 0.2% w/v casamino acids, 24 mg/L pantothenate, 80 mg/L L-lysine, 10% v/v OADC supplement). OADC supplement contained 0.5 g/L oleic acid, 50 g/L albumin fraction V, 20 g/L dextrose, 40 mg/L catalase, and 8.5 g/L NaCl. Cultures were inoculated from frozen glycerol stocks or from agar plates and cultured at 37° C. with shaking for one week. For each experiment, the optical density at 600 nm ($OD_{600}$) was measured in a spectrophotometer and cultures were diluted to the desired $OD_{600}$.

The number of bacterial cells was estimated by plating serial dilutions of cultures with known $OD_{600}$ onto agar plates. After 3-5 weeks of growth at 37° C., individual colonies were counted to obtain the conversion between $OD_{600}$ and bacterial concentration (colony-forming units [CFU]/mL). $OD_{600}$ of 1 represented ~$3\times10^8$ CFU/mL.

FLASH Measurements

All experiments were performed in triplicate unless indicated otherwise. All chemiluminescence assays were performed in white, opaque flat-bottom 384-well plates. Luminescence was measured in a Biotek Cytation™ 3 plate reader at 37° C. unless indicated otherwise. For all experiments, luminescence measurements began immediately after the addition of FLASH probe. For each sample, luminescence measurements from the first hour were summed to yield integrated luminescence.

Hip1 Activity Measurement with FLASH Probe

Recombinant Hip1 was purified as previously described (Lentz et al., 2016). Hip1 enzyme was aliquoted in Hip1 buffer (0.01% Triton X-100 in PBS). Into each well of a white flat-bottom 384-well plate, 5 μL of 225 mM FLASH probe in 1:1 DMSO/Hip1 buffer (final concentration 10 μM) were added to 40 μL of two-fold series dilutions of recombinant Hip1 (final concentrations 12.5-0.05 nM).

FLASH Probe Titration

Into each well of a white flat-bottom 384-well plate, 5 μL 9×FLASH probe in 1:1 DMSO/Hip1 buffer (final concentration 45-0 μM) was added to 40 μL of 3 nM Hip1 in Hip1 buffer (final enzyme concentration: 2.7 nM).

Enzyme Inhibition with CSL157

Into each well of a white flat-bottom 384-well plate, 2.5 μL of CSL157 ((9H-fluoren-9-yl)methyl (S)-1-(3-(2-bromoethoxy)-4-chloro-1-oxo-1H-isochromen-7-ylcarbamoyl)-5-aminopentylcarbamate; compound 5 in Lentz et al., 2016) in DMSO (two-fold dilution series for final concentrations of 15-0.015 μM) or DMSO were preincubated with 37.5 μL of 3 nM Hip1 in Hip1 at 37° C. for 30 min. After incubation, 5 μL of 225 μM FLASH probe in 1:1 DMSO/Hip1 buffer (final concentration 25 μM) were added.

Detection of Bacterial Cells

Cultures were grown until reaching $OD_{600}$ 0.4-1.0 and were then diluted in growth medium to reach the desired $OD_{600}$. Into each well of a white flat-bottom 384-well plate, 5 μL of 225 μM FLASH probe in 1:1 DMSO/Hip1 buffer (final concentration 25 μM) were added to 20 μL of diluted bacterial culture. Experiments with Mtb $mc^2$6020 and all Nontuberculous Mycobacteria were performed in a Biotek Cytation™ 3 plate reader as described above. Experiments with Mtb H37Rv were performed in a Molecular Devices SpectraMax M2 plate reader at 25° C.

CellTiter-Blue Viability Measurements

Into each well of a clear, 96-well plate, 20 μL of CellTiter-Blue was added to 100 μL of bacterial culture. The plate was incubated for 24 h at 37° C. and then fluorescence was measured in a Biotek Cytation™ 3 (ex. 560 nm, em. 590 nm).

Antibiotic Killing Experiments

Cultures of Mtb $mc^2$6020 were grown to $OD_{600}$ 0.2-0.4, diluted into culture medium to a final $OD_{600}$ 0.2, and then split into separate cultures for each antibiotic treatment condition. Rifampicin stocks were made in PBS at 100× each desired final concentration. Rifampicin was added to each culture and cultures were incubated for up to nine days at 37° C. with shaking. At each measurement time point, aliquots of culture were removed and measured by FLASH as described above or by CellTiter-Blue. For all time points, a sample of untreated cell culture was heat-killed by incubation at 95° C. for 10 min. For dose-response curves, measurements were normalized to the no-cell controls (0% viability) and to the untreated controls (100% viability).

Results

Figure 2A:
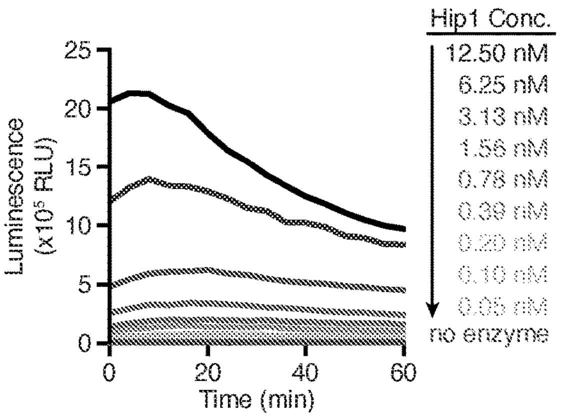
FIGS. 2A-2E show that FLASH detects pmols of active Hip1 enzyme. (2A) Time course of luminescent signal emitted by FLASH upon incubation with recombinant Hip1 enzyme in vitro. Higher Hip1 concentrations yield higher luminescent signals, and no luminescent signal is produced in the absence of enzyme. (2B) Luminescent signal from 2A was integrated to yield integrated luminescence (IL) over time, which represents the total light output generated over the course of the experiment. (2C) Total IL values after 1 h for each tested concentration of Hip1 enzyme. The limit of detection (LOD) is ~2 pmol of Hip1 enzyme (n=3, one-way ANOVA with multiple comparisons to the no-enzyme control: *, $p<0.001$). (2**D) Initial cleavage rates for Hip1 incubated with various FLASH concentrations. Values were fit to a nonlinear regression to estimate the Michaelis-Menten constants for FLASH. (2E) Inhibition of Hip1 activity as detected by FLASH. Hip1 was pre-incubated with the inhibitor compound CSL157 for 30 min at 37° C. Values were fit to a two-parameter logistic model to estimate the $IC_{50}$. For all experiments, the measurements were subtracted by the mean IL value for a no-enzyme control.
Figure 2B:
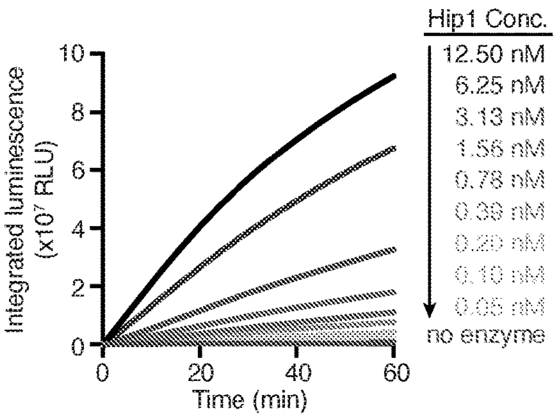
Figure 2C:
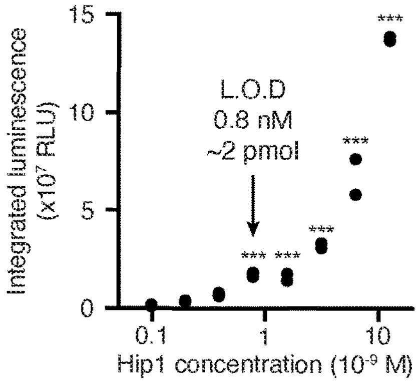
Figure 2D:
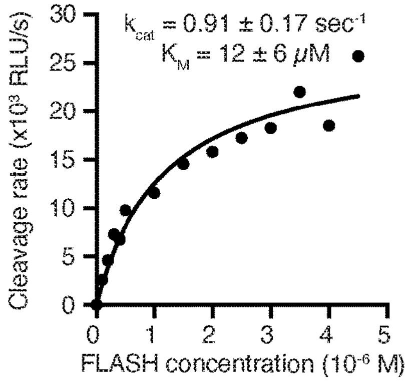
Figure 2E:
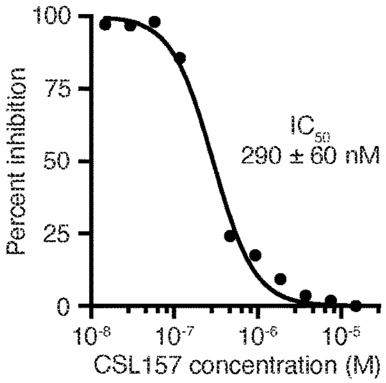

FIGS. 2A-2E show that FLASH detects pmols of active Hip1 enzyme. FIG. 2A shows time course of luminescent signal emitted by FLASH upon incubation with different concentrations of recombinant Hip1 enzyme in vitro. Higher Hip1 concentrations yield higher luminescent signals, and no luminescent signal is produced in the absence of enzyme. FIG. 2B shows the luminescent signal shown in 2A, integrated to yield integrated luminescence (IL) over time, representing the total light output generated over the course of the experiment. FIG. 2C shows total IL values after 1 h for each tested concentration of Hip1 enzyme. The limit of detection (LOD) is ~2 pmol of Hip1 enzyme. FIG. 2D shows initial cleavage rates for Hip1 incubated with various FLASH concentrations. Values were fit to a nonlinear regression to estimate the Michaelis-Menten constants for FLASH. FIG. 2E shows inhibition of Hip1 activity as detected by FLASH. Hip1 was pre-incubated with the inhibitor compound CSL157 for 30 min at 37° C. Values were fit to a two-parameter logistic model to estimate the $IC_{50}$. For all experiments, the measurements were subtracted by the mean IL value for a no-enzyme control.

Figure 3A:
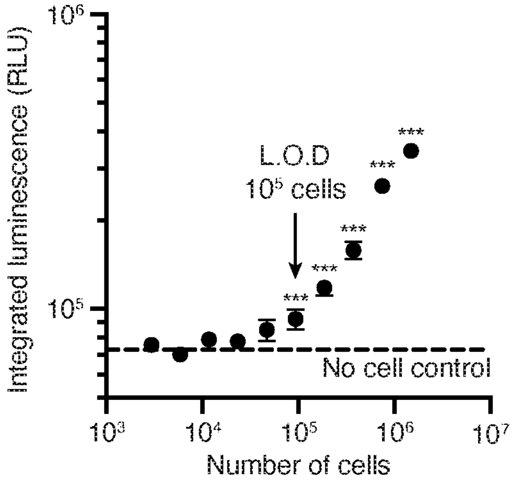
FIGS. 3A-3B show that FLASH detects Mtb cells in culture. Mtb strain $mc^2$6020 (3A) or H37Rv (3B) was incubated with FLASH for 1 h. The LOD for both strains is ≤100,000 cells. Error bars show standard deviation (n=7, one-way ANOVA with multiple comparisons to the no-cell control: ***, $p<0.001$).
Figure 3B:
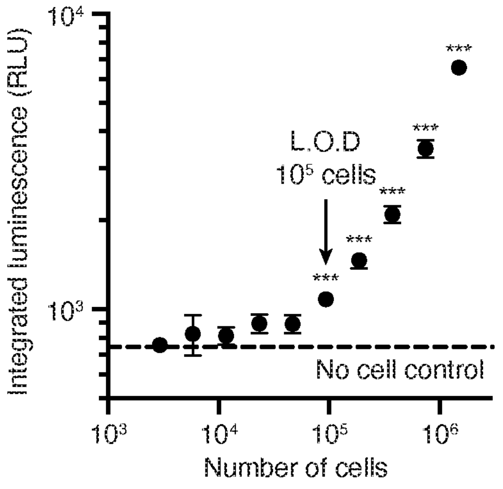
Figure 5A:
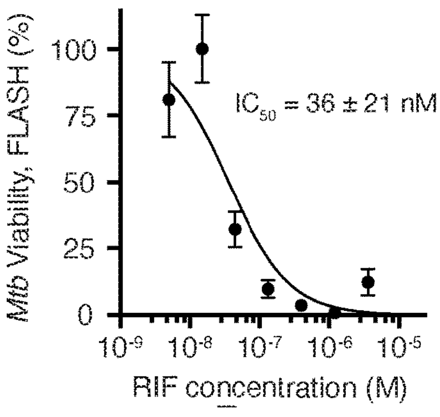
FIGS. 5A-5E show that flash detects antibiotic killing of Mtb. Mtb cultures were treated with rifampicin (RIF) for up to nine days. Samples were removed throughout the treatment period and incubated with FLASH for 1 h, or with CellTiter-Blue (CTB) for 24 h. (5A-5B) dose response for killing by RIF as measured by the FLASH probe (5A) or CTB (5B) (mean±s.d., n=3) after 7 days of RIF treatment. Data were normalized to DMSO (100% viability) and 10 μm RIF (0% viability) and fit to a two-parameter logistic function. $IC_{50}$ values are reported as 95% confidence intervals. (5C-5D) time course of (5C) $mc^2$6020 or (5D) H37Rv (WT) Mtb and RpoB H526D mutant Mtb (RpoB), treated with DMSO or the critical concentration of RIF (1.2 μm). For each day, the RIF- and DMSO-treated conditions were compared via an independent t-test (n=3; *, $p<0.001$; , $p<0.01$; *, $p<0.05$). (5E) Luminescent signal from H37Rv (WT) or RpoB after 6 days of culture in the presence or absence of RIF. Samples were compared to the WT Mtb strain treated with RIF via one-way ANOVA with Dunnett's test (***, $p<0.001$).
Figure 5B:
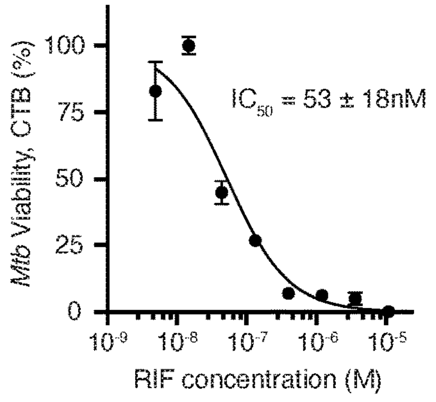
Figure 5C:
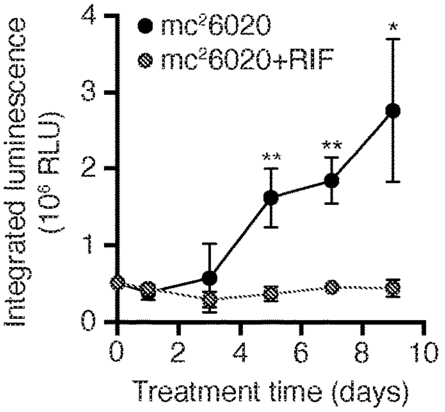
Figure 5D:
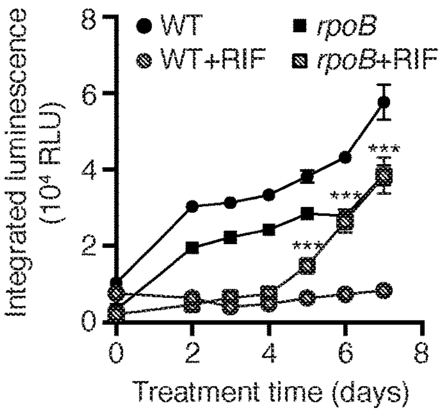
Figure 5E:
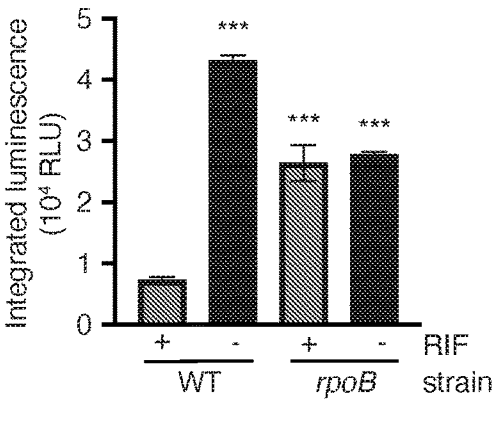

FIGS. 3A-3B show that FLASH detects Mtb cells in culture. Mtb strain $mc^2$6020 (3A) or H37Rv (3B) was incubated with FLASH for 1 h. The LOD, i.e., the lowest number of bacterial cells that can be detected by the probe, for both strains is ≤100,000 cells.

FIGS. 4A-4C show that FLASH is more sensitive to Mtb compared to common nontuberculous mycobacteria. FIG. 4A shows percent identities between Hip1 homologues found in NTM species and the Mtb sequence, and protein sequence alignments for regions surrounding the three active-site residues (Ser228, Asp463, and His490). FIGS. 4B-4C show IL values for millions (4B) or thousands (4C) of cells of each species incubated with FLASH for 1 h.

FIGS. 5A-5D show that FLASH detects antibiotic killing of Mtb. Mtb cultures were treated with rifampicin (RIF) for up to nine days. Samples were removed throughout the treatment period and incubated with FLASH for 1 h, or with CellTiter-Blue (CTB) for 24 h. (5A-5B) Dose response for killing by RIF as measured by the FLASH probe (D) or CTB (E) after 7 days of RIF treatment. Data were normalized to DMSO (100% viability) and 10 μM RIF (0% viability) and fit to a two-parameter logistic function. $IC_{50}$ values are reported as 95% confidence intervals. (5C-5D) Time course of (5C) $mc^2$6020 or (5D) H37Rv Mtb and RpoB H526D mutant Mtb (rpoB) treated with DMSO or the critical concentration of RIF (1.2 μM). For each day, the RIF- and DMSO-treated conditions were compared via an independent t-test. (5E) Luminescent signal from H37Rv or rpoB after 6 d of culture in the presence or absence of RIF. Samples were compared to the H37Rv Mtb strain treated with RIF via one-way ANOVA with Dunnett's test.

REFERENCES

Chi, C.; Du, Y.; Ye, J.; Kou, D.; Qiu, J.; Wang, J.; Tian, J.; Chen, X. *Theranostics* 2014, 4(11), 1072-1084

Hananya, N.; Reid, J. P.; Green, O.; Sigman, M. S.; Shabat, D., Rapid chemiexcitation of phenoxy-dioxetane luminophores yields ultrasensitive chemiluminescence assays. *Chem. Sci.,* 2019, 10(5), 1380-1385

Lentz, C. S.; Ordonez, A. A.; Kasperkiewicz, P.; La Greca, F.; P'Donoghue, A. J.; Schulze, C. J.; Powers. J. C.; Craik, C. S.; Drag, M.; Jain, S. K.; Bogyo, M. *ACS Infect Dis,* 2016, 2, 807-815

Mieog, J. S.; Troyan, S. L.; Hutteman, M.; Donohoe, K. J.; van der Vorst, J. R.; Stockdale, A.; Liefers, G. J.; Choi, H. S.; Gibbs-Strauss, S. L.; Putter, H.; Gioux, S.; Kuppen, P. J.; Ashitate, Y.; Lowik, C. W.; Smit, V. T.; Oketokoun, R.; Ngo, L. H.; van de Velde, C. J.; Frangioni, J. V.; Vahrmeijer, A. L. *Annals of surgical oncology* 2011, 18, 2483-2491

Troyan, S. L.; Kianzad, V.; Gibbs-Strauss, S. L.; Gioux, S.; Matsui, A.; Oketokoun, R.; Ngo, L.; Khamene, A.; Azar, F.; Frangioni, J. V. *Annals of surgical oncology* 2009, 16, 2943-2952

What is claimed is:

1. A compound of the formula Ia or Ib:

Ia

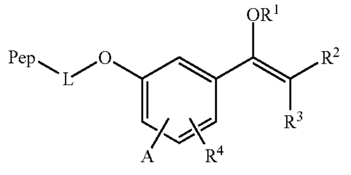

Ib

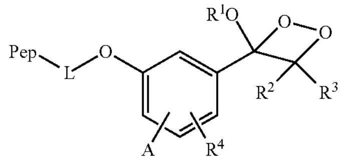

wherein $R^1$ is selected from the group consisting of $(C_1-C_{18})$alkyl and $(C_3-C_7)$cycloalkyl;

$R^2$ and $R^3$ each independently is selected from the group consisting of a branched $(C_3-C_{18})$alkyl and $(C_3-C_7)$ cycloalkyl, or $R^2$ and $R^3$ together with the carbon atom to which they are attached form a fused, spiro or bridged cyclic or polycyclic ring;

$R^4$ is H, or halogen attached either ortho or para to the —O-L-Pep group;

A is a π* acceptor group of the formula $$-(CH=CH)_r-E,$$

attached either ortho or para to the —O-L-Pep group, wherein r is an integer of 1 to 6, and E is:

(a) —CN, —COOH, or —COO($C_1$-$C_{18}$)alkyl optionally interrupted in the alkylene chain with one or more —O— groups or substituted with one or more groups each independently selected from the group consisting of —OH, —COOH, halogen, and —$NH_2$;

(b) a group of the formula

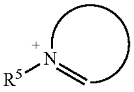
or
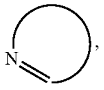

denoting a mono- or polycyclic, aromatic or nonaromatic ring system comprising the moiety

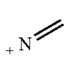
or
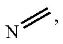

respectively, as a ring member, and linked to the alkenylene chain of group A via any atom which is a member of said mono- or polycyclic, aromatic or nonaromatic ring system, provided that a delocalized x-system extends from the nitrogen atom of

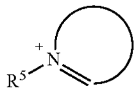
or
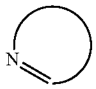

via the alkenylene chain of group A to the central aromatic ring of the compound of formula Ia or Ib, wherein said mono- or polycyclic, aromatic or nonaromatic ring system is optionally substituted with one or more groups each independently selected from the group consisting of halogen, —OH, —CN, —$SO_3H$ or a salt thereof, —COOH or a salt thereof, —COO—($C_1$-$C_{18}$)alkyl, ($C_1$-$C_6$)alkyl, ($C_2$-$C_6$)alkenyl, ($C_2$-$C_6$)alkynyl, a polyethylene glycol chain, and a polypropylene glycol chain, and wherein $R^5$ is H, —$O^-$, ($C_1$-$C_8$)alkyl, ($C_2$-$C_8$)alkenyl, or ($C_2$-$C_8$)alkynyl, wherein said ($C_1$-$C_8$)alkyl, ($C_2$-$C_8$)alkenyl and ($C_2$-$C_8$)alkynyl each is optionally substituted with one or more groups each independently selected from the group consisting of —OH, —COOH, halogen, and —$NH_2$, and optionally interrupted with one or more —O— or —CO— groups; or (c) a group of the formula

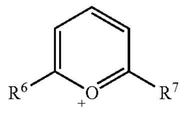

linked to the alkenylene chain of group A via a carbon atom of the pyrylium moiety, wherein $R^6$ and $R^7$ each independently is selected from the group consisting of H, ($C_1$-$C_6$)alkyl, ($C_2$-$C_6$)alkenyl, ($C_2$-$C_6$)alkynyl, and ($C_3$-$C_7$)cycloalkyl;

L is a linker of the formula:

L1

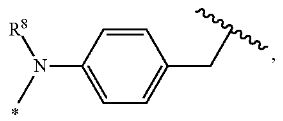

L2

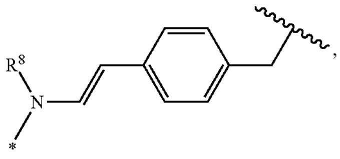

L3

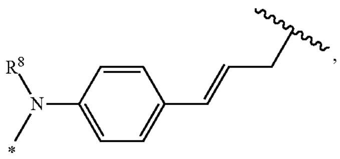

L4

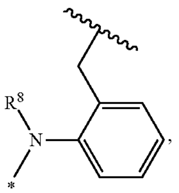

L5

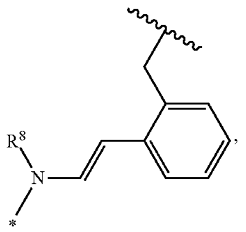

L6

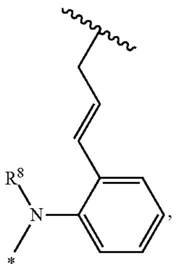

L7

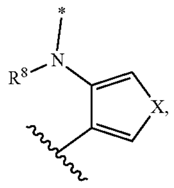

L8

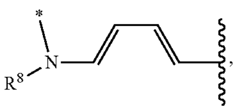
and

-continued

L9

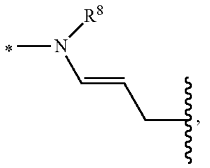

optionally substituted at the aromatic or heteroaromatic ring with one or more substituents each independently selected from the group consisting of $(C_1-C_{18})$alkyl and $(C_3-C_7)$cycloalkyl, wherein X is S, O, or $NR^8$; $R^8$ each independently is H or $(C_1-C_{18})$alkyl; and the asterisk represents the point of attachment to the group Pep; and Pep is a *Mycobacterium tuberculosis* (Mtb)-specific protease cleavable peptide linked via a carboxylic group thereof and optionally acetylated at its alpha amino acid.

2. The compound of claim 1, wherein:

(i) $R^1$ is $(C_1-C_8)$alkyl; or (ii) $R^2$ and $R^3$ together with the carbon atom to which they are attached form a fused, spiro or bridged polycyclic ring; or (iii) $R^4$ is halogen attached ortho or para to the —O-L-Pep group; or (iv) A is π* acceptor group attached either ortho or para to the —O-L-Pep group and selected from the group consisting of —CH═CH—CN; —CH═CH—COOH; —CH═CH—COO$(C_1-C_{18})$alkyl optionally interrupted in the alkylene chain with one or more —O— groups; and a group of the formula:

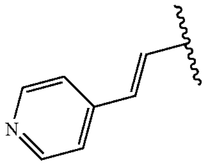

,

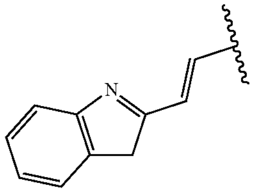

,

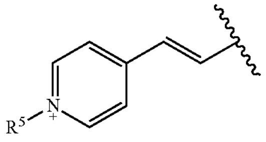

,

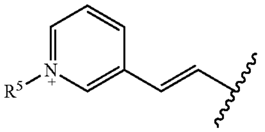

,

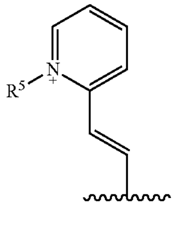

,

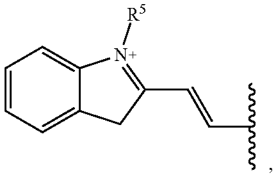

,

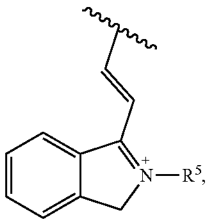

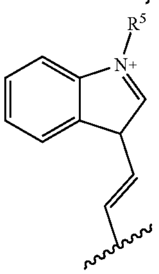

,

-continued

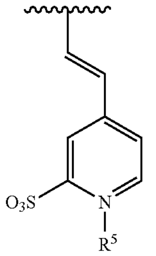

,

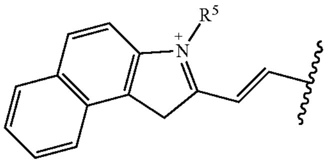

,

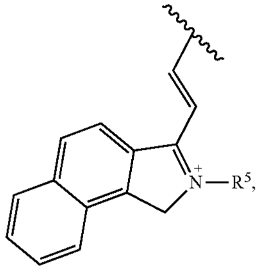

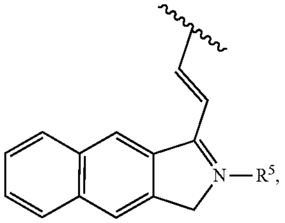

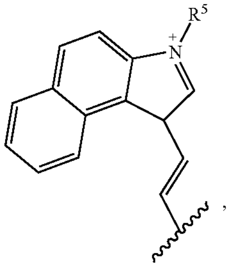

,

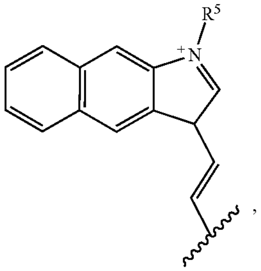

,

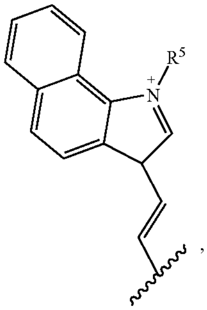

,

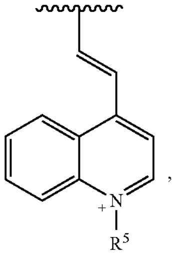

,

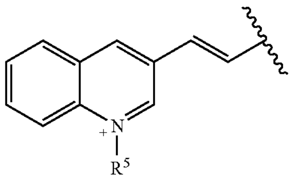

,

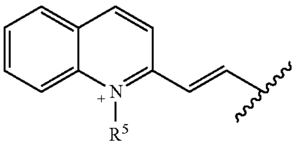

,

-continued
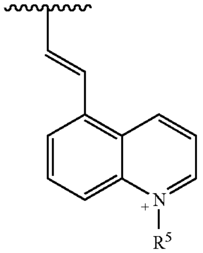,
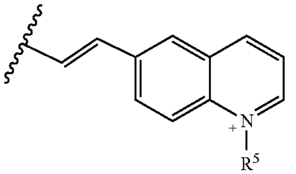,
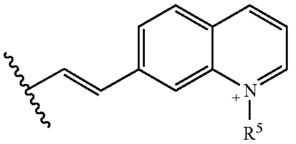,
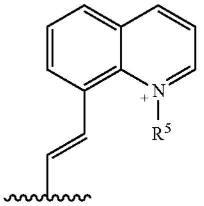,
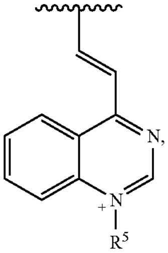,
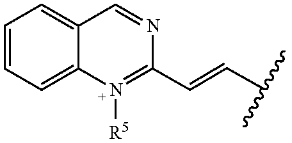,
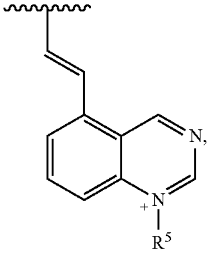,
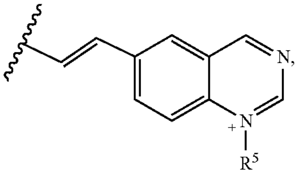,
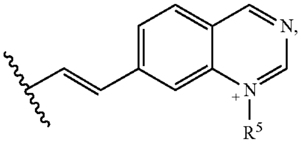,
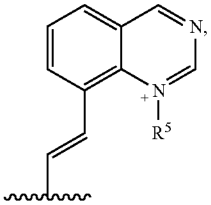,
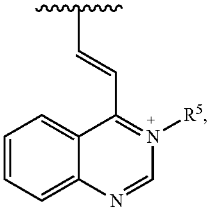,
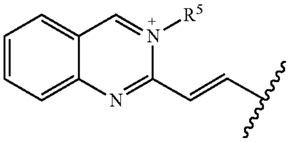,
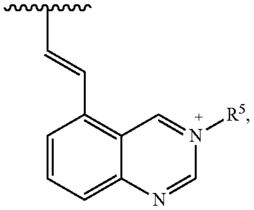,
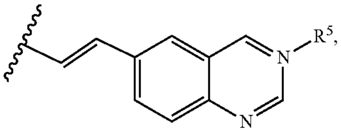,
-continued
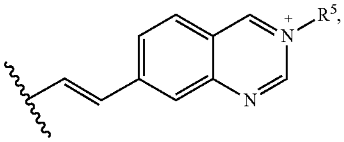,
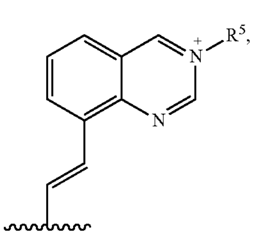,
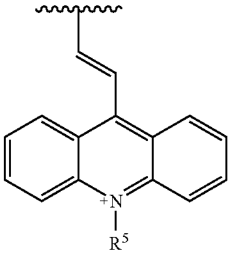,
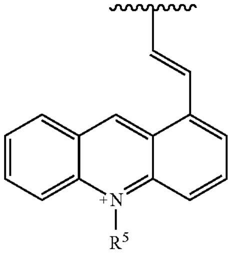,
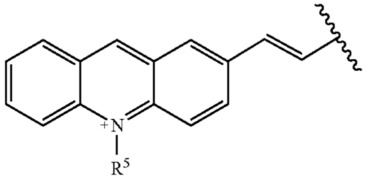,
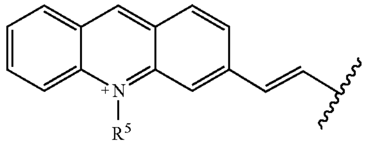,
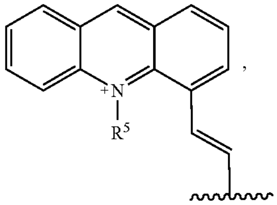,
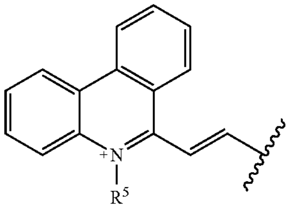,
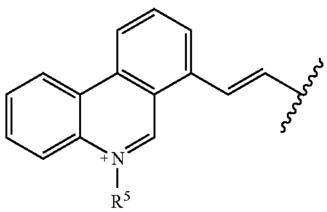, -continued

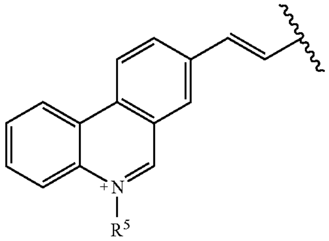

,

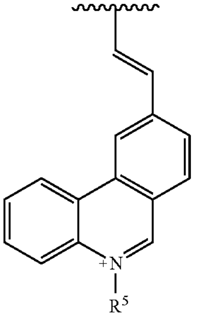

,

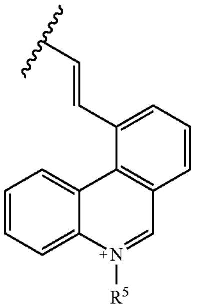

,

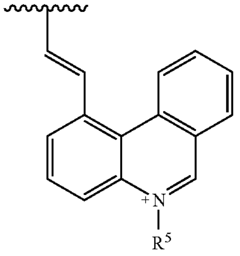

,

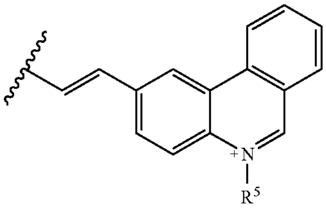

,

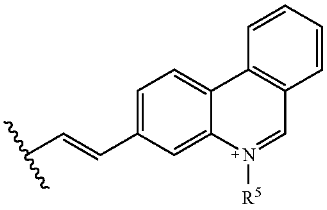

,

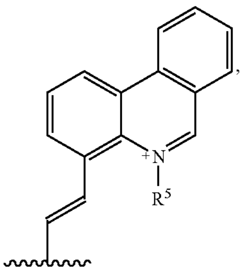

, or

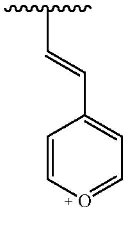

, optionally substituted with one or more groups each independently selected from the group consisting of halogen, —OH, —CN, —$SO_3H$ or a salt thereof, —COOH or a salt thereof, —COO—($C_1$-$C_{18}$)alkyl, ($C_1$-$C_6$)alkyl, ($C_2$-$C_6$)alkenyl, ($C_2$-$C_6$)alkynyl, a polyethylene glycol chain, and a polypropylene glycol chain, wherein $R^5$ is H, —$O^-$, or ($C_1$-$C_8$)alkyl optionally substituted with one or more groups each independently selected from the group consisting of —OH, —COOH, halogen, and —$NH_2$, and optionally interrupted with one or more —O— or —CO— groups; or (v) L is a linker of the formula L1, L2 or L3.

3. The compound of claim 2, wherein $R^2$ and $R^3$ together with the carbon atom to which they are attached form adamantyl.

4. The compound of claim 2, wherein A is selected from the group consisting of —CH═CH—CN; —CH═CH—COOH; —CH═CH—COO($C_1$-$C_{18}$)alkyl optionally interrupted in the alkylene chain with one or more —O— groups; and a group of the formula:

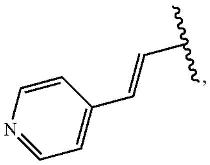

,

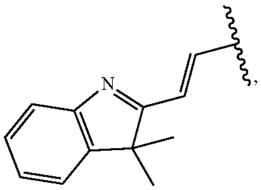

,

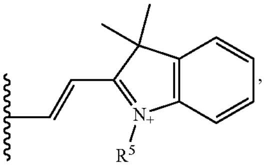

,

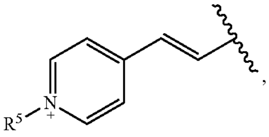

,

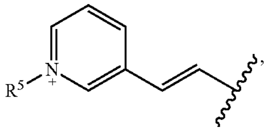

,

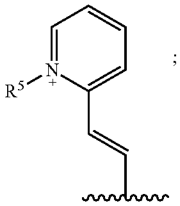

;

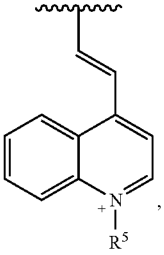

, or

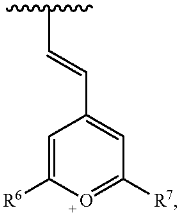

wherein $R^5$ is H, —$O^-$, methyl, or ($C_1$-$C_8$)alkyl substituted with —COOH;

$R^6$ and $R^7$ each independently is ($C_1$-$C_6$)alkyl; and when the respective position is available for substitution, the aromatic ring is optionally substituted with one or two —$COO^-$ or —$SO_3$ groups in ortho position to the positively charged nitrogen atom.

5. The compound of claim 4, wherein A is selected from the group consisting of —CH═CH—CN, —CH═CH—COOH, and —CH═CH—COO($C_1$-$C_{18}$)alkyl optionally interrupted in the alkylene chain with one or more —O— groups.

6. The compound of claim 1, wherein:

$R^1$ is ($C_1$-$C_8$)alkyl;

$R^2$ and $R^3$ together with the carbon atom to which they are attached form a fused, spiro or bridged polycyclic ring;

$R^4$ is halogen attached ortho or para to the —O-L-Pep group;
A is a π* acceptor group attached either ortho or para to the —O-L-Pep group and selected from the group consisting of —CH═CH—CN; —CH═CH—COOH; —CH═CH—COO($C_1$-$C_{18}$)alkyl optionally interrupted in the alkylene chain with one or more —O— groups; and a group of the formula:
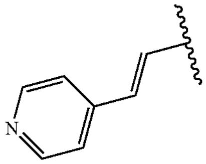,
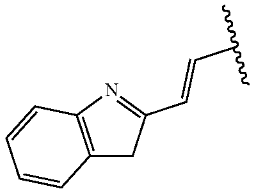,
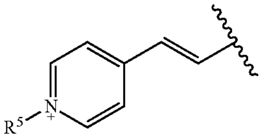,
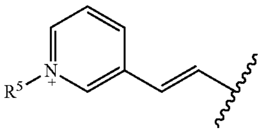,
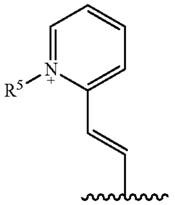,
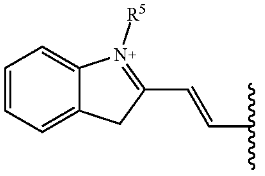,
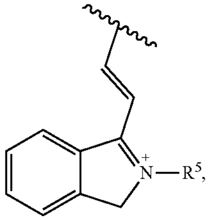
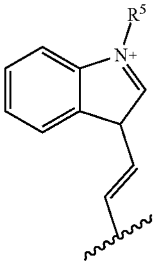,
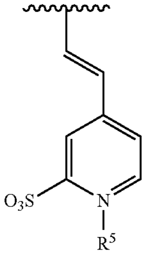,
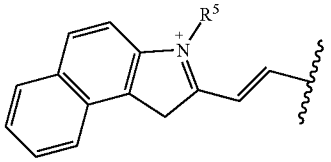,
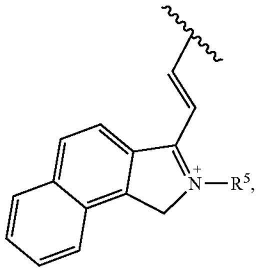
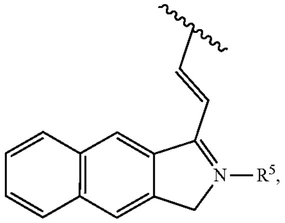
-continued
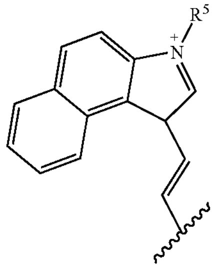,
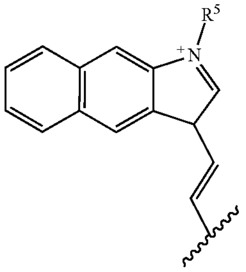,
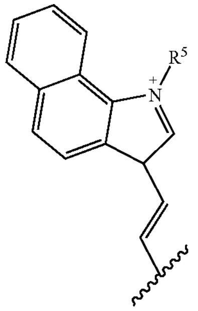,
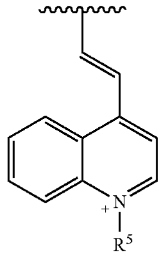,
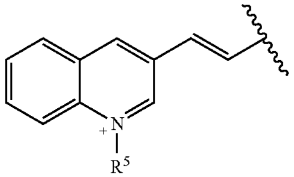,
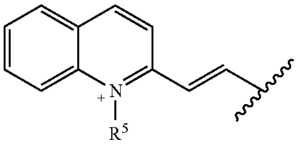,
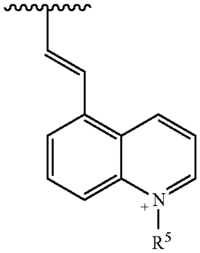,
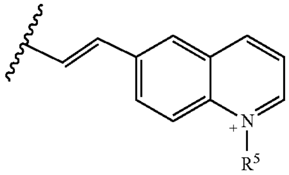,
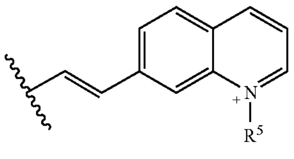,
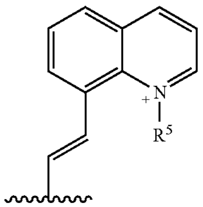,
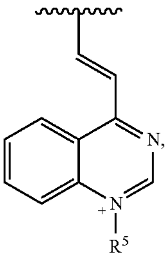
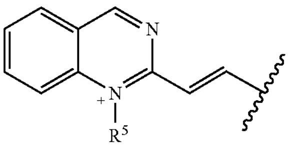, -continued
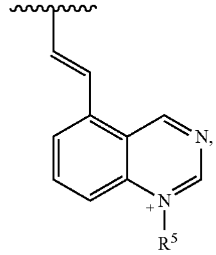
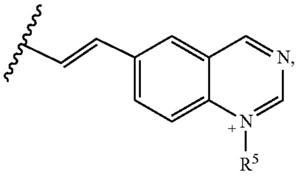
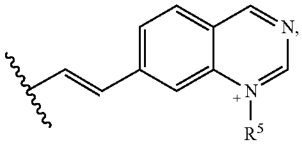
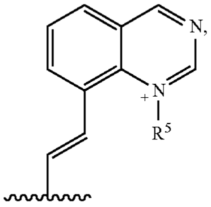
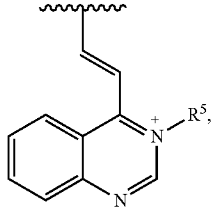
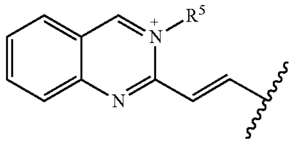
,
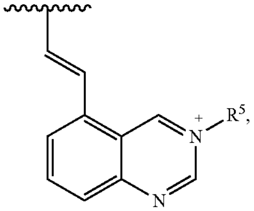
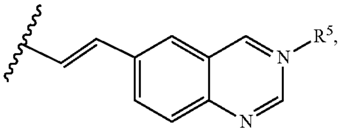
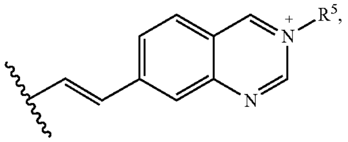
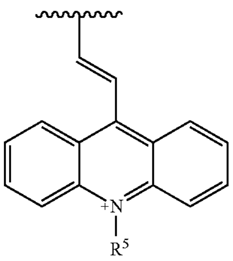
,
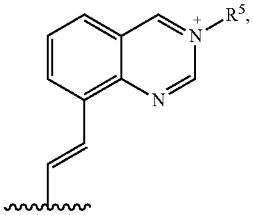
-continued
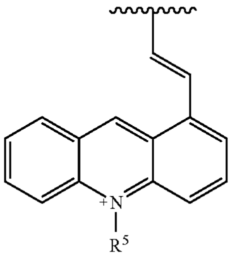
,
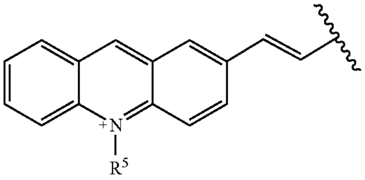
,
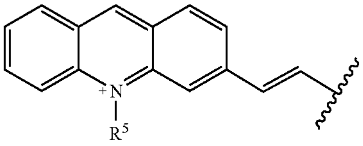
,
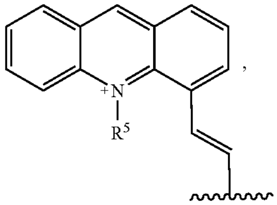
,
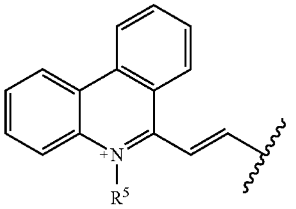
,
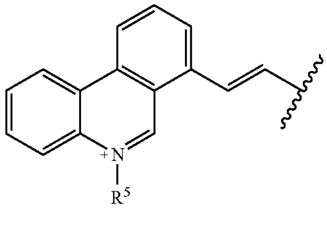
,
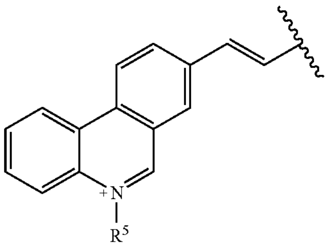
, -continued

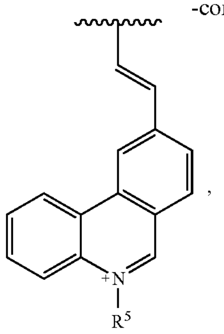

,

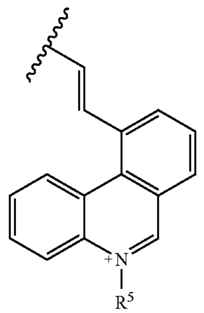

,

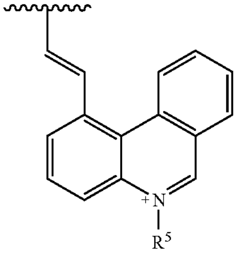

,

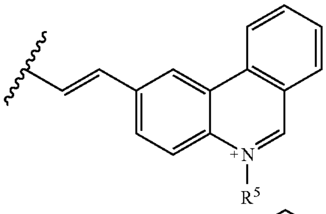

,

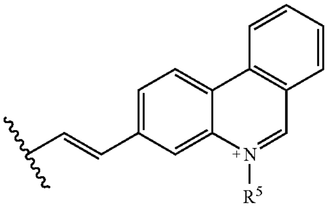

,

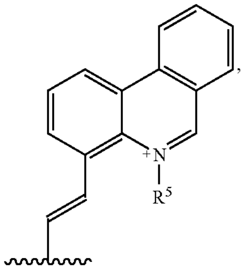

, or

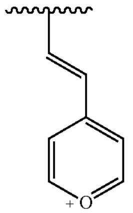

, optionally substituted with one or more groups each independently selected from the group consisting of halogen, —OH, —CN, —$SO_3H$ or a salt thereof, —COOH or a salt thereof, —COO—($C_1$-$C_{18}$)alkyl, ($C_1$-$C_6$)alkyl, ($C_2$-$C_6$)alkenyl, ($C_2$-$C_6$)alkynyl, a polyethylene glycol chain, and a polypropylene glycol chain, wherein $R^5$ is H, —$O^-$, or ($C_1$-$C_8$)alkyl optionally substituted with one or more groups each independently selected from the group consisting of —OH, —COOH, halogen, and —$NH_2$, and optionally interrupted with one or more —O— or —CO— groups; and L is a linker of the formula L1, L2 or L3.

7. The compound of claim 6, wherein A is selected from the group consisting of —CH═CH—CN; —CH═CH—

COOH; —CH═CH—COO($C_1$-$C_{18}$)alkyl optionally interrupted in the alkylene chain with one or more —O— groups; and a group of the formula:

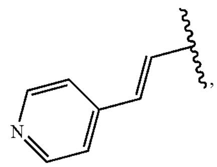

,

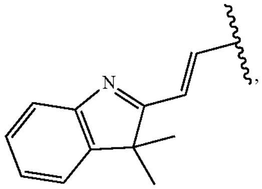

,

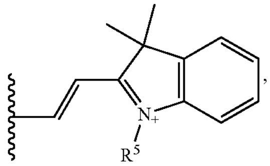

,

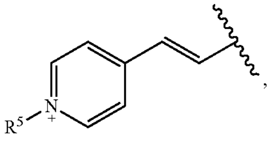

,

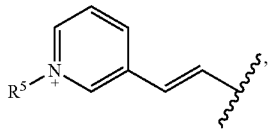

,

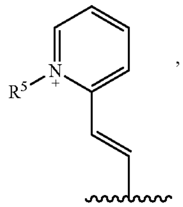

,

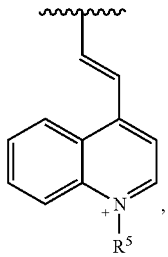

, or

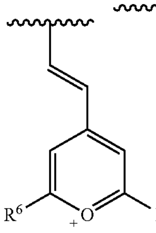

, wherein $R^5$ is H, —$O^-$, methyl, or ($C_1$-$C_8$)alkyl substituted with —COOH;

$R^6$ and $R^7$ each independently is ($C_1$-$C_6$)alkyl; and when the respective position is available for substitution, the aromatic ring is optionally substituted with one or two —$COO^-$ or —$SO_3$ groups in ortho position to the positively charged nitrogen atom.

8. The compound of claim 7, wherein $R^1$ is methyl; $R^2$ and $R^3$ together with the carbon atom to which they are attached form adamantyl; $R^4$ is halogen attached ortho to the —O-L-Pep group; A is selected from the group consisting of —CH═CH—CN, —CH═CH—COOH, and —CH═CH—COO($C_1$-$C_{18}$)alkyl optionally interrupted in the alkylene chain with one or more —O— groups, attached ortho to the —O-L-Pep group; and L is a linker of the formula L1, L2 or L3, wherein $R^8$ is H.

9. The compound of claim 8, wherein A is selected from the group consisting of —CH═CH—CN, —CH═CH—COOH, —CH═CH—$COOCH_3$, —CH═CH—COOC$(CH_3)_3$, and —CH═CH—COO$[(CH_2)_2—O]_4$—$CH_3$.

10. The compound claim 1, wherein Pep is a peptide of the formula $Xaa_5$-$Xaa_4$-$Xaa_3$-$Xaa_2$-$Xaa_1$-, wherein $Xaa_1$ is an amino acid linked via the carboxylic group thereof to group L; $Xaa_2$ is Lys; $Xaa_3$ and $Xaa_4$ each is an amino acid; and $Xaa_5$ is either absent or represents a sequence of one or more amino acids, provided that either $Xaa_4$ or the terminal amino acid of $Xaa_5$, when present, is acetylated at its alpha amino group.

11. The compound of claim 10, wherein $Xaa_1$ is an aliphatic amino acid; and $Xaa_3$ is a non-natural aromatic amino acid.

12. The compound of claim 11, wherein $Xaa_1$ is Leu or Gln; $Xaa_3$ is 4ClPhe; and $Xaa_4$ is Igl, (benzyl) cysteine, or Asp.

13. The compound of claim 12, wherein $Xaa_5$ is absent.

14. The compound of claim 13, wherein $R^1$ is methyl; $R^2$ and $R^3$ together with the carbon atom to which they are attached form adamantyl; $R^4$ is $C_1$ attached ortho to the —O-L-Pep group; A is-CH═CH—CN, —CH═CH—COOH, —CH═CH—$COOCH_3$, —CH═CH—COOC$(CH_3)_3$, or —CH═CH—COO$[(CH_2)_2$—O$]_4$—$CH_3$, attached ortho to the —O-L-Pep group; L is a linker of the formula L1, L2 or L3, wherein $R^8$ is H; and Pep is a peptide of the formula $Xaa_5$-$Xaa_4$-$Xaa_3$-$Xaa_2$-$Xaa_1$-, wherein $Xaa_1$ is Leu; $Xaa_2$ is Lys; $Xaa_3$ is 4ClPhe; $Xaa_4$ is Igl; and $Xaa_5$ is absent.

15. The compound of claim 14, selected from the group consisting of compounds Ib-1a, Ib-1b (MTCL), Ib-1c, Ib-1d and Ib-1e Ib-1a

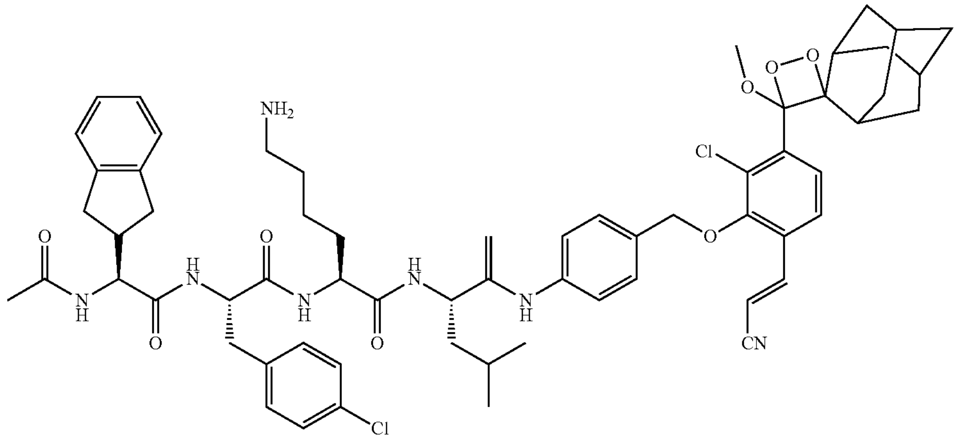

Ib-1b (MTCL)

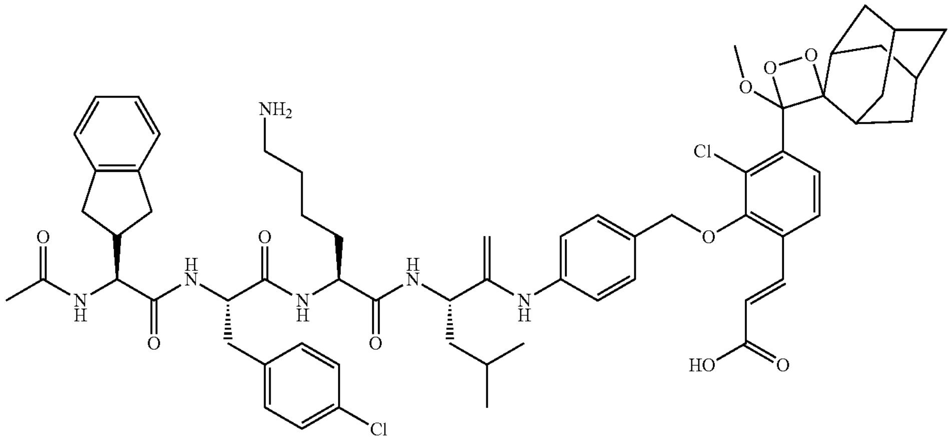

Ib-1c

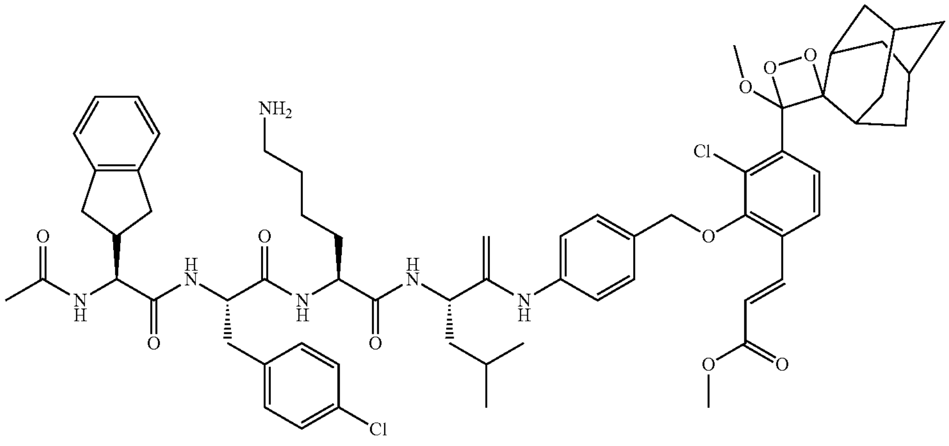

-continued

Ib-1d

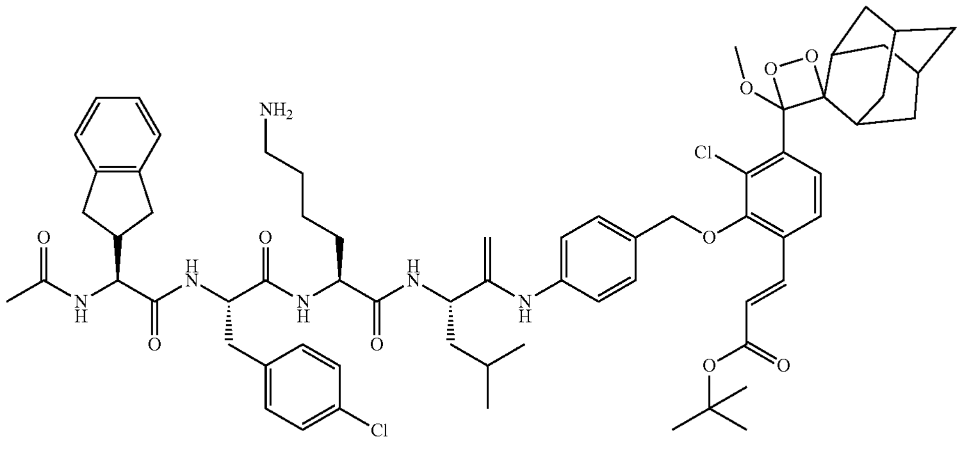

Ib-1e

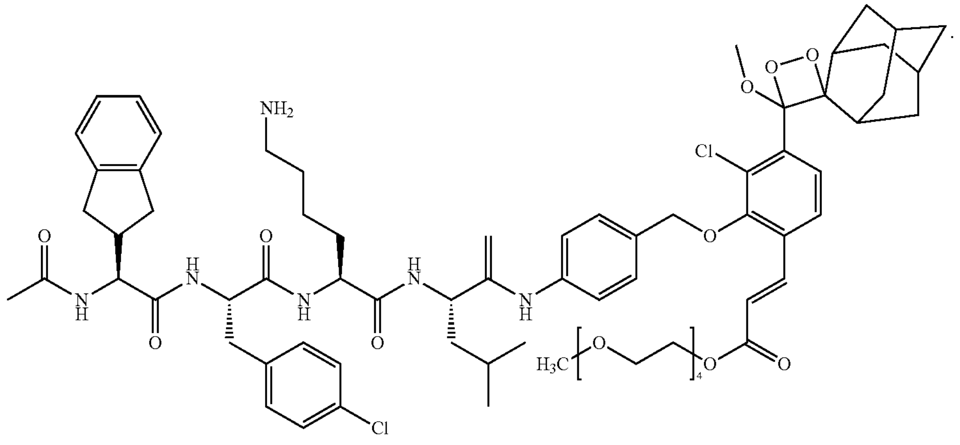

16. A composition comprising a compound according to claim 1 and a carrier.

17. A method for determining the presence, or measuring the level, of *Mycobacterium tuberculosis* (Mtb)-specific protease in a sample, said method comprising:

(i) contacting said sample with a compound according to claim 1, wherein in the presence of Mtb-specific protease in said sample, said Mtb-specific protease cleavable peptide is cleaved from the compound of formula Ia/Ib, thereby generating an unstable phenolate-dioxetane compound, which is then decomposed through a chemiexcitation process to produce an excited intermediate that decays to its ground-state through emission of light; and (ii) imaging said sample to detect the emission of light.

18. A method for assessing the susceptibility of *Mycobacterium tuberculosis* (Mtb) present in a sample to an antibiotic drug, said method comprising:

(i) contacting said sample with a compound according to claim 1 at a time period after contacting said sample with said antibiotic drug, wherein in the presence of Mtb-specific protease in said sample, said Mtb-specific protease cleavable peptide is cleaved from the compound of formula Ia/Ib, thereby generating an unstable phenolate-dioxetane compound, which is then decomposed through a chemiexcitation process to produce an excited intermediate that decays to its ground-state through emission of light; and (ii) imaging said sample to detect the emission of light, wherein a decrease in the intensity of emission detected in step (ii) as compared to a reference level detected after contacting said sample with said compound without contacting said sample with said antibiotic drug indicates that said Mtb is susceptible to said antibiotic drug.

19. The method of claim 17, wherein said sample is a biological sample selected from the group consisting of a bodily fluid, an aqueous solution in which said bodily fluid is dissolved, and a tissue biopsy sample.

20. The method of claim 17, wherein said sample is contacted with a compound wherein $R^1$ is methyl; $R^2$ and $R^3$ together with the carbon atom to which they are attached form adamantyl; $R^4$ is $C_1$ attached ortho to the —O-L-Pep group; A is —CH═CH—CN, —CH═CH—COOH, —CH═CH—$COOCH_3$, —CH═CH—$COOC(CH_3)_3$, or —CH═CH—$COO[(CH_2)_2$—$O]_4$—$CH_3$, attached ortho to the —O-L-Pep group; L is a linker of the formula L1, L2 or L3, wherein $R^8$ is H; and Pep is a peptide of the formula $Xaa_5$-$Xaa_4$-$Xaa_3$-$Xaa_2$-$Xaa_1$-, wherein $Xaa_1$ is Leu; $Xaa_2$ is Lys; $Xaa_3$ is 4ClPhe; $Xaa_4$ is Igl; and $Xaa_5$ is absent.

21. The method of claim 20, wherein said compound is selected from the group consisting of compounds Ib-1a, Ib-1b (MTCL), Ib-1c, Ib-1d and Ib-1e set forth below:

Ib-1a
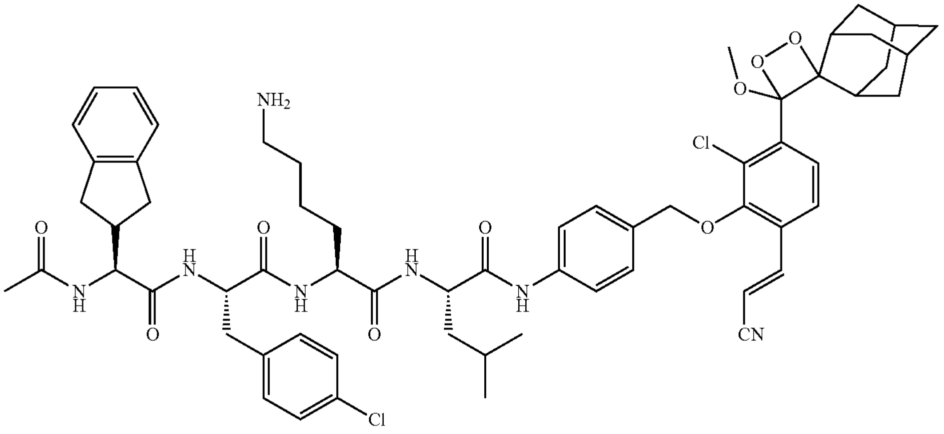
Ib-1b
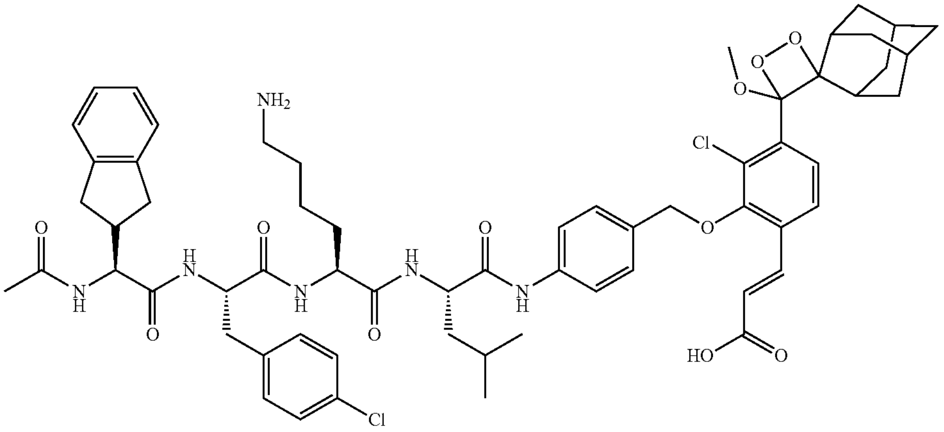
(MTCL)
Ib-1c
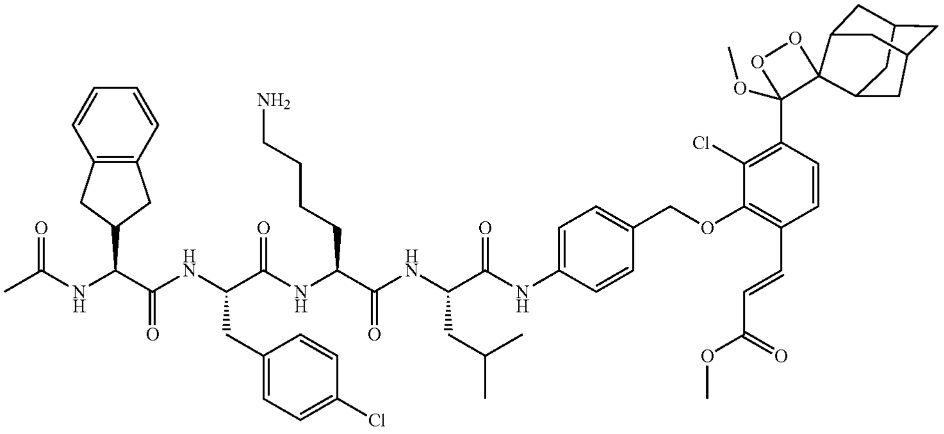

-continued

Ib-1d

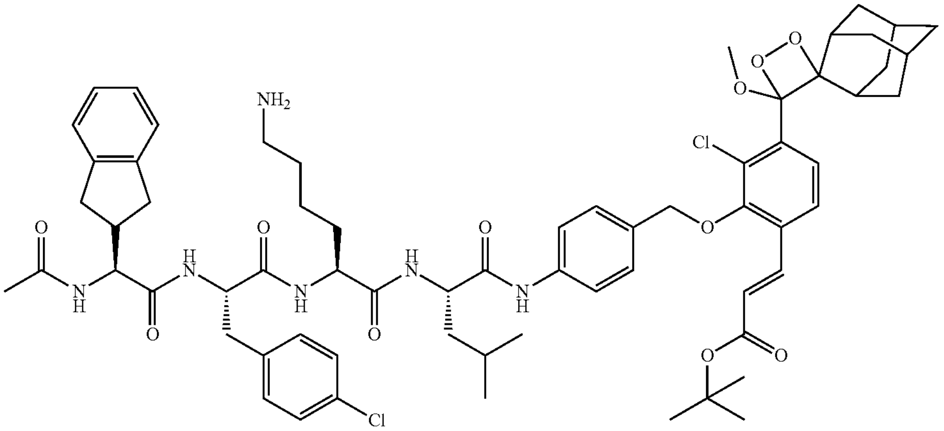

Ib-1e

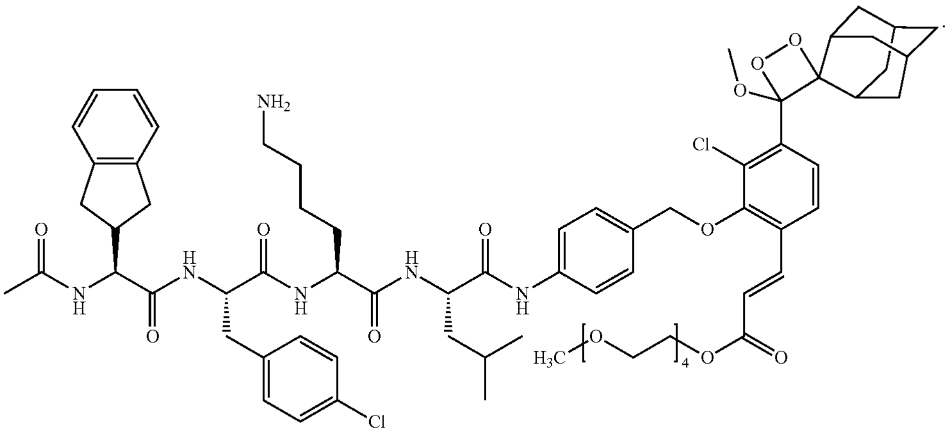

22. The method of claim 18, wherein said sample is a biological sample selected from the group consisting of a bodily fluid, an aqueous solution in which said bodily fluid is dissolved, and a tissue biopsy sample.

23. The method of claim 18, wherein said sample is contacted with a compound wherein $R^1$ is methyl; $R^2$ and $R^3$ together with the carbon atom to which they are attached form adamantyl; $R^4$ is $C_1$ attached ortho to the —O-L-Pep group; A is-CH═CH—CN, —CH═CH—COOH, —CH═CH—$COOCH_3$, —CH═CH—$COOC(CH_3)_3$, or —CH═CH—$COO[(CH_2)_2$—$O]_4$—$CH_3$, attached ortho to the —O-L-Pep group; L is a linker of the formula L1, L2 or L3, wherein $R^8$ is H; and Pep is a peptide of the formula $Xaa_5$-$Xaa_4$-$Xaa_3$-$Xaa_2$-$Xaa_1$-, wherein $Xaa_1$ is Leu; $Xaa_2$ is Lys; $Xaa_3$ is 4ClPhe; $Xaa_4$ is Igl; and $Xaa_5$ is absent.

24. The method of claim 23, wherein said compound is selected from the group consisting of compounds Ib-1a, Ib-1b (MTCL), Ib-1c, Ib-1d and Ib-1e set forth below:

Ib-1a

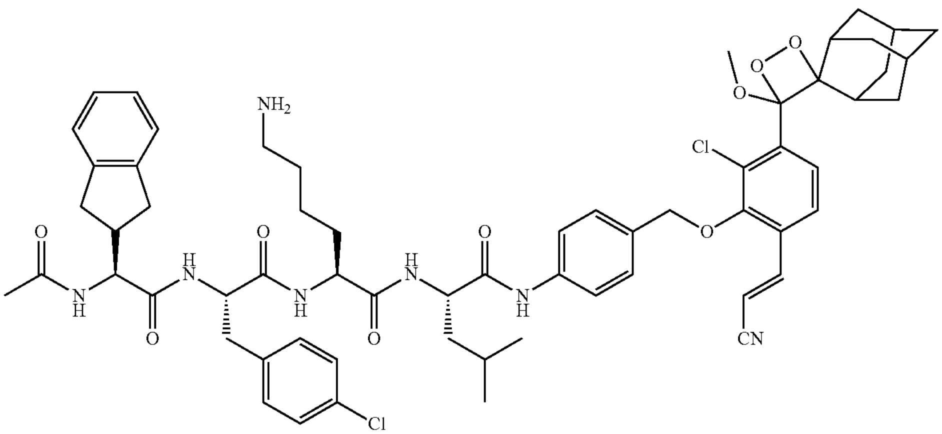

-continued
Ib-1b
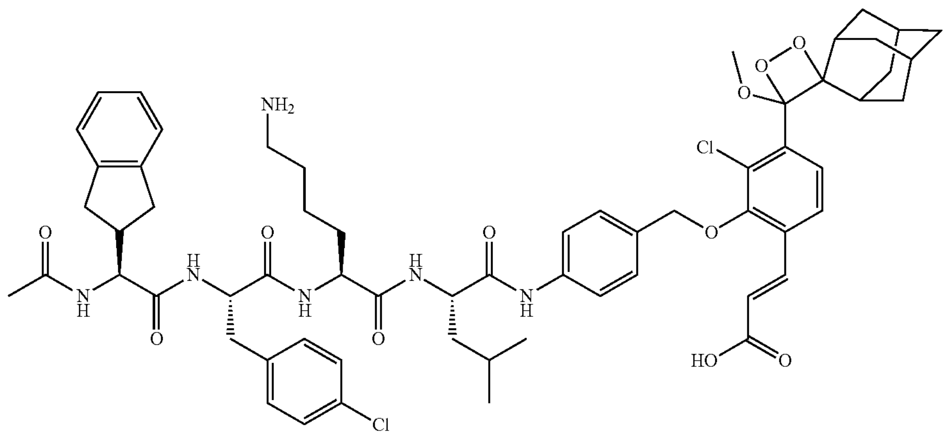
(MTCL)
Ib-1c
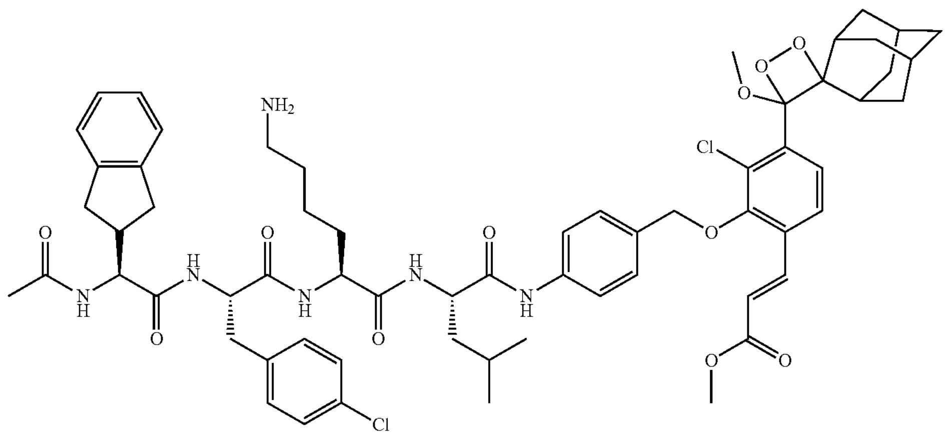
Ib-1d
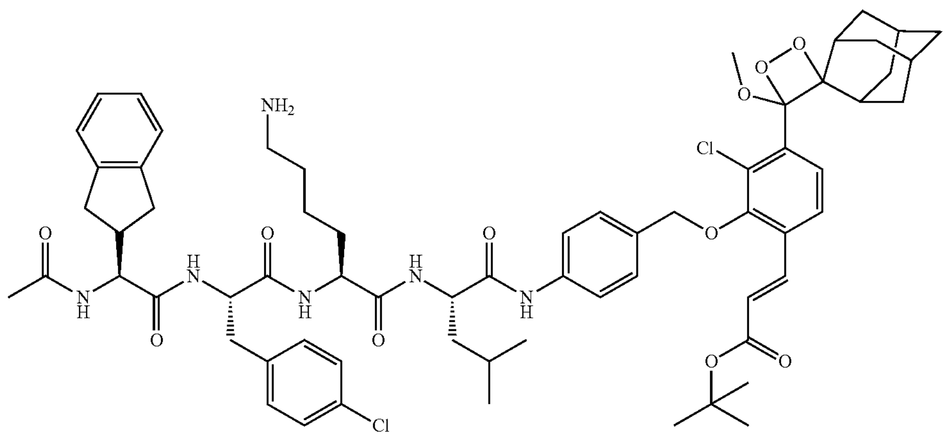

-continued
Ib-1e
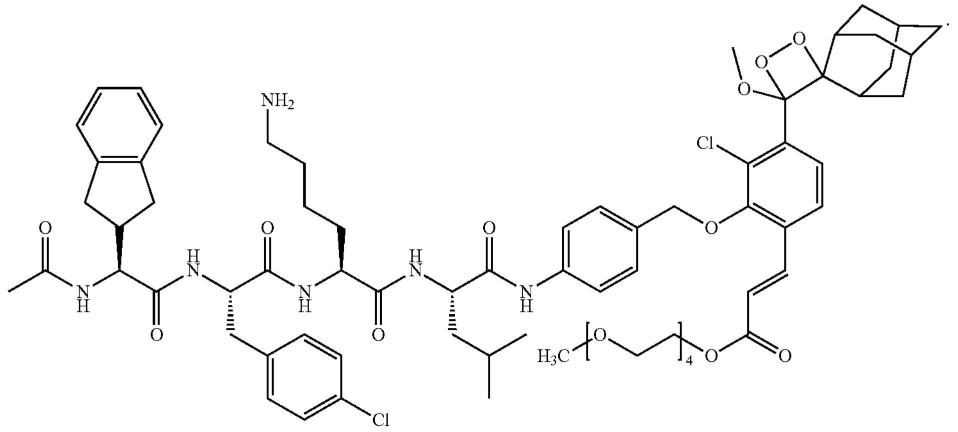
25. The compound of claim 14, wherein A is —CH═CH—COOH attached ortho to the —O-L-Pep group; L is a linker of the formula L1 wherein $R^8$ is H, of the formula:
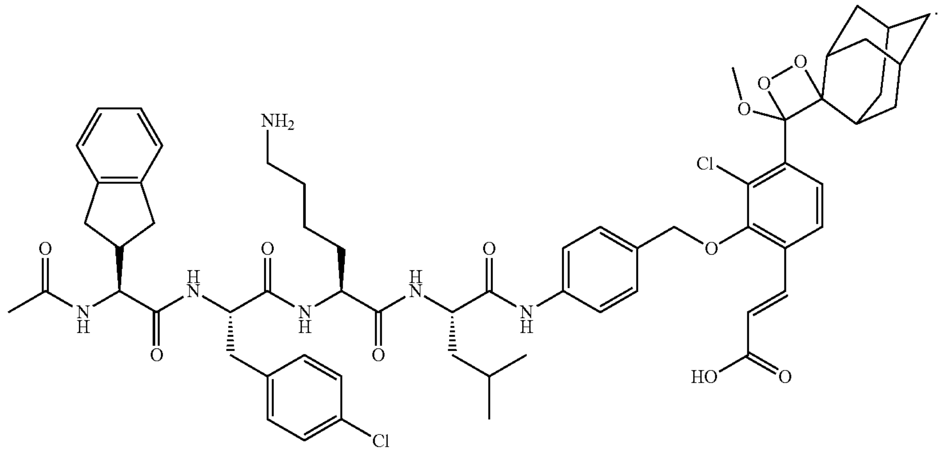 [SMILES: COC1(c2ccc(/C=C/C(=O)O)c(OCc3ccc(NC(=O)[C@H](CC(C)C)NC(=O)[C@H](CCCCN)NC(=O)[C@H](Cc4ccc(Cl)cc4)NC(=O)[C@@H](NC(C)=O)C4Cc5ccccc5C4)cc3)c2Cl)OOC12C1CC3CC(C1)CC2C3]
26. The compound of claim 1, wherein said Mtb-specific protease cleavable peptide is linked via the alpha-carboxylic group thereof.
* * * * *